(12) United States Patent
Hakamata et al.

(10) Patent No.: US 7,123,756 B2
(45) Date of Patent: Oct. 17, 2006

(54) METHOD AND APPARATUS FOR STANDARDIZED FLUORESCENCE IMAGE GENERATION

(75) Inventors: Kazuo Hakamata, Kaisei-machi (JP); Tomonari Sendai, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 534 days.

(21) Appl. No.: 10/132,738

(22) Filed: Apr. 26, 2002

(65) Prior Publication Data

US 2002/0168096 A1    Nov. 14, 2002

(30) Foreign Application Priority Data

Apr. 27, 2001   (JP)   .............................. 2001-132421

(51) Int. Cl.
*G06K 9/00*   (2006.01)

(52) U.S. Cl. ........................ 382/128; 382/254; 378/44

(58) Field of Classification Search ........ 382/128–134, 382/254; 378/44–50
See application file for complete search history.

(56) References Cited

U.S. PATENT DOCUMENTS

| | | | |
|---|---|---|---|
| 5,827,190 A * | 10/1998 | Palcic et al. ................. | 600/476 |
| 6,826,424 B1 * | 11/2004 | Zeng et al. ................. | 600/476 |
| 2002/0161282 A1 * | 10/2002 | Fulghum ..................... | 600/160 |
| 2005/0065406 A1 * | 3/2005 | Cline et al. ................. | 600/160 |

\* cited by examiner

*Primary Examiner*—Jingge Wu
*Assistant Examiner*—Charles Kim
(74) *Attorney, Agent, or Firm*—Sughrue Mion, PLLC

(57) ABSTRACT

A correction function is calculated based on a reference image formed of reflected light reflected upon the irradiation of a predetermined living tissue, for which a diseased state is known, with a reference light. This correction function is employed to administer distance correction on calculated standardized values based on fluorescence images to which an offset has been added, to correct the fluctuations of the calculated standardized values caused by the distance between living tissue and the distal end of a fluorescence endoscope, thereby generating a corrected standardized fluorescence image.

22 Claims, 10 Drawing Sheets

METHOD AND APPARATUS FOR STANDARDIZED FLUORESCENCE IMAGE GENERATION

BACKGROUND OF THE INVENTION

1. Field of the Invention

The present invention relates to a method and apparatus for standardized image generation which detects reradiated light of mutually different wavelength bandwidths, generated from a living tissue by irradiation thereof by light, as images; adds a desired offset to at least one of the images of mutually different bandwidths; and generates a standardized image based on the ratio between the mutually different images, at least one of which the offset has been added to.

2. Description of the Related Art

When a living tissue is irradiated by excitation light within an excitation light wavelength range of pigment existing within a living organism, normal tissue and diseased tissue emit fluorescent light of different intensities. There has been proposed a fluorescence detection apparatus that takes advantage of this phenomenon by irradiating a living tissue with excitation light of a predetermined wavelength range, and recognizing the location and region of infiltration of diseased tissue by detecting the fluorescent light emitted by the pigment existing therein.

Generally, when irradiated with excitation light, normal tissue emits strong fluorescence as indicated by the solid line in the graph of FIG. 10, whereas fluorescence weaker than that of normal tissue is emitted from diseased tissue, as indicated by the broken line in the graph of FIG. 10. Therefore, by measuring the intensity of fluorescence, a judgment can be made as to whether living tissue is normal or in a diseased state.

Further, there has been proposed a method in which fluorescence caused by excitation light is imaged by an imaging element, and a judgment is made as to whether living tissue is normal or in a diseased state by displaying a fluorescence image corresponding to the intensity of the fluorescence. With regard to this technology, as there are concavities and convexities in living tissue, the intensity of excitation light irradiated on the living tissue is not uniform. Consequently, the intensity of the fluorescence emitted from the living tissue decreases in proportion to the square of the distance between a light source and the living tissue. In addition, the intensity of the fluorescence emitted from the living tissue decreases in proportion to the square of the distance between a fluorescence detection means and the living tissue as well. Therefore, there are cases in which fluorescence of a stronger intensity is received from diseased tissue closer to the light source or the fluorescence detection means than from normal tissue further therefrom. Consequently, it is not possible to accurately discriminate the tissue state of living tissue based solely on information regarding the intensity of fluorescence caused by excitation light. In order to reduce such inaccuracies, there has been proposed a method in which fluorescence images are obtained based on fluorescence intensities of two mutually different wavelength bandwidths (a narrow bandwidth in the vicinity of 480 nm, and a wide bandwidth ranging from the vicinity of 430 nm to the vicinity of 730 nm), the ratio between the two fluorescence images is derived by division, then a standardized fluorescence image is generated based on the divided value. That is, a method of standardized fluorescence image generation based on the difference of the shape of the fluorescence spectra which reflects the tissue state of an organism has been proposed. Further, a method in which color information is assigned to the divided value of the fluorescence images of different wavelength bandwidths, and indicating the diseased state of living tissue by differences in color shown in a color image has been proposed. Still further, a method in which a near infrared light, which is uniformly absorbed by various living tissues, is irradiated on living tissue as a reference light, a reference image based on the intensity of the light reflected by the living tissue upon irradiation thereof with the reference light is detected, brightness information is assigned to the reference image, and the brightness image obtained thereby is synthesized with the aforementioned color image, thereby showing an image having a three dimensional feel which reflects the contour of the tissue as well, has been proposed.

In addition, in the case that a standardized fluorescence image is generated based on the divided value of fluorescence images of different wavelength bandwidths, the fluorescence intensity from the living tissue used for the standardization calculation is minute. Therefore, the standardized fluorescence image based on this fluorescence intensity has an extremely low S/N ratio. In order to ameliorate this problem, the adding of an offset to at least one of the fluorescence images of different wavelength bandwidths when the aforementioned divided value is calculated, thereby improving the S/N ratio of the standardized fluorescence image, has been proposed.

When deriving a divided value by adding an offset as described above, a favorable S/N ratio can be obtained by making the value of the offset large. However, the fluorescence intensity changes greatly depending on the distance between the detection means and the living tissue. Therefore, if the offset is made too large, cases arise in which living tissue far from the detection means and living tissue close to the detection means have greatly different divided values even when their diseased state is the same. Consequently, the discrimination between diseased tissue and normal tissue becomes difficult. As an example, the relationship between the divided values and the aforementioned distances of a predetermined normal tissue and a predetermined diseased tissue is shown in the graph of FIG. 8. The divided values were obtained by dividing a narrow bandwidth fluorescence image by a wide bandwidth fluorescence image to which an offset was added (narrow bandwidth fluorescence image/(wide bandwidth fluorescence image+offset)). Values of 5, 10, 15, and 20 were utilized for the offset, and the divided values for the normal tissue are indicated by the outlined symbols, while the divided values for the diseased tissue are indicated by the solid symbols. As shown in the figure, the divided value changes according to the aforementioned distance. It can be seen that the larger the offset value, the difference between the divided values of the normal tissue and the diseased tissue decrease as the aforementioned distance increases, and discrimination therebetween becomes difficult. Conversely, if the offset value is small, changes in the divided value according to distance is less significant. However, a problem arises that an effect whereby the S/N ratio of the standardized fluorescence image is improved is not sufficiently obtained. Further, standardized fluorescence images of a predetermined living tissue based on the above described divided value are shown in FIGS. 9A and 9B. FIG. 9A shows a standardized fluorescence image wherein the distance between the detection means and the living tissue is large, and FIG. 9B shows a standardized fluorescence image wherein the aforementioned distance is small. Note that the offset value in these cases is 20, and in each image, the portions that are comparatively darker than their surroundings indicate diseased portions. As shown in the figure, although it is necessary that the large distance image (far image) and the small distance image (close image) display their normal tissue portions and their diseased tissue portions at the same brightnesses, respectively, the far image is darker than the close image as a whole. In addition, there is little contrast in the far image between the normal tissue portion and the diseased tissue portion, making discrimination therebetween difficult.

SUMMARY OF THE INVENTION

The present has been developed in view of the aforementioned problems. It is an object of the present invention to provide a method and apparatus for standardized image generation that generates a standardized image from images of mutually different wavelength bandwidths, at least one of which a desired offset has been added to, wherein a uniform calculated standardized value, which is not dependent on a distance between living tissue and a detection means, can be obtained even in a case when this distance changes.

The first method of standardized image generation of the present invention comprises the steps of: irradiating a living tissue with light; detecting images of mutually different wavelength bandwidths based on reradiated light generated from the living tissue by the irradiation with the light with an image detection means; adding a desired offset to at least one of the images of mutually different wavelength bandwidths; and generating a standardized image based on the ratio of the images of mutually different wavelength bandwidths, at least one of which a desired offset has been added to; wherein a predetermined correction function is employed for performing a distance correction on the standardized image, which corrects for the amount of fluctuation of the standardized image caused by the distance between the living tissue and the image detection means, thereby generating a corrected standardized image.

Here, the aforementioned "image detection means" refers to, for example, with regard to a fluorescence endoscope that detects fluorescent light generated by living tissue due to irradiation thereof by excitation light, components including but not limited to: an endoscope insertion portion to be inserted within a body; an imaging element that obtains an image of fluorescent light guided thereto from the endoscope insertion portion; and the light guide portion that guides the light to the imaging element. Separate imaging elements and light guide portions may be provided for each of the images of mutually different wavelength bandwidths, or a single imaging element and a single light guide portion may be commonly used therefor.

The aforementioned "adding a desired offset to at least one of said images of mutually different wavelength bandwidths" refers to adding an offset value to each pixel value of each image. By adding the offset value to the image, deviations in the pixel values of the standardized image after the standardizing calculation will be decreased, and the S/N ratio of the standardized image can be improved. The offset value need not be added to the entirety of the image. The offset value may be added solely to the dark portions of the image, i.e., portions where the S/N ratio is low. That is, it is favorable that an offset value of a size that improves the S/N ratio of the standardized image, thereby improving the accuracy in the recognition of a tissue state, is added when the standardizing calculation is performed based on the ratio of the images.

The aforementioned "ratio of the images" refers to the ratio of each pair of pixels having corresponding coordinates in each image, of the images of mutually different wavelength bandwidths. The aforementioned "generating a standardized image based on the ratio of said images" refers to performing division or a similar standardizing calculation on each pair of pixels having corresponding coordinates, then generating as the standardized image an image which has as its pixel values the values obtained by the standardizing calculation.

The aforementioned "distance between the living tissue and the image detection means" refers to the distance that actually influences the size of the pixel value of the detected image. However, for example, with regard to a fluorescence endoscope, this distance refers to the distance between living tissue, which is the target of measurement, and the tip of the endoscope insertion portion of the fluorescence endoscope. Further, in the case that an excitation light emitting means for irradiating the living tissue with excitation light moves in positional relationship with the living tissue, this motion causes a difference in the pixel values of the fluorescence image. Therefore, the aforementioned distance includes the distance between the excitation light emitting means and the living tissue as well.

The aforementioned "amount of fluctuation of the standardized image" refers to the amount of fluctuation in the pixel values of the standardized image.

The aforementioned "performing a distance correction on the standardized image, which corrects for the amount of fluctuation of the standardized image caused by the distance between the living tissue and the image detection means" refers to correcting the pixel values of the standardized image so that they do not fluctuate depending on the aforementioned distance.

The second method of standardized image generation of the present invention comprises the steps of: irradiating a living tissue with excitation light; detecting fluorescence images of mutually different wavelength bandwidths based on fluorescent light generated from the living tissue by the irradiation with the excitation light with a fluorescence image detection means; adding a desired offset to at least one of the fluorescence images of mutually different wavelength bandwidths; and generating a standardized fluorescence image based on the ratio of the fluorescence images of mutually different wavelength bandwidths, at least one of which a desired offset has been added to; wherein a predetermined correction function is employed for performing a distance correction on the standardized image, which corrects for the amount of fluctuation of the standardized fluorescence image caused by the distance between the living tissue and the fluorescence image detection means, thereby generating a corrected standardized fluorescence image.

The fluorescence images of mutually different wavelength bandwidths may be a narrow bandwidth fluorescence image and a wide bandwidth fluorescence image.

The correcting function may be calculated based on at least one of a wide bandwidth fluorescence image and a narrow bandwidth fluorescence image of a living tissue for which a diseased state is known.

The correcting function may be calculated based on a reference image, obtained by irradiating a predetermined living tissue, for which a diseased state is known, with a reference light; and detecting a reference image formed of the reflected light reflected by said living tissue with a reference image detection means.

Here, the aforementioned "reference image detection means" refers to, for example, with regard to a fluorescence endoscope, components including but not limited to: an endoscope insertion portion to be inserted within a body; an imaging element that obtains an image of reference light guided thereto from the endoscope insertion portion; and the light guide portion that guides the light to the imaging element. Note that it is desirable that the reference image detection means and the fluorescence image detection means share a common endoscope insertion portion and light guide portion. However, because the wavelength bandwidths differ, optical filters must be provided to select the wavelength bandwidths for each image. In addition, in the case that a common imaging element is to be employed, imaging may be performed by shifting the timing of exposures.

In the case that the correction function is calculated based on the reference image, it is desirable that the distance between the reference image detection means and the living tissue, and the distance between the fluorescence image detection means and the living tissue be made equal.

The correction function may be expressed by Equation (1) below, and the corrected standardized fluorescence image may be calculated by Equation (2) below.

(nir+os2)/nir  Equation 1:

{n/(w+os1)}×{(nir+os2)/nir}  Equation 2:

Here, n is the narrow bandwidth fluorescence image; w is the wide bandwidth fluorescence image; nir is the reference image; os1 is the offset, os2 is the correction coefficient, os2=os1×knir/kw; knir is the reference image divided by the distance between the living tissue and the reference image detection means; and kw is the wide bandwidth fluorescence image divided by the distance between the living tissue and the fluorescence image detection means.

In the equations above, n, w, and nir represent the pixel values of the narrow bandwidth fluorescence image, the wide bandwidth fluorescence image, and the reference image, respectively. Also, knir represents the pixel values of the reference image divided by the distance between the living tissue and the reference image detection means. In addition, kw represents the pixel values of the wide bandwidth fluorescence image divided by the distance between the living tissue and the fluorescence image detection means. That is, kw represents the pixel values of the wide bandwidth fluorescence image per unit distance. Further, os2 is to be calculated by substituting the offset, knir, and kw in the equation above.

The aforementioned os2 may be calculated based on values of knir and kw when imaging a normal portion of living tissue with the reference image detection means and the fluorescence image detection means.

The aforementioned os2 may also be calculated based on values of knir and kw when imaging a diseased portion of living tissue with the reference image detection means and the fluorescence image detection means.

The aforementioned os2 may alternatively calculated by dividing the degree of disease progression of a diseased portion of living tissue into s steps; obtaining values of knir and kw when the living tissue is imaged at each of the s steps; and calculating os2 based on each knir and kw.

Further, an s number of corrected standardized fluorescence images, which are to become reference corrected standardized fluorescence images, may be calculated by employing an s number of the correction functions based on the os2 corresponding to each living tissue of s steps to perform distance correction to the standardized fluorescence images for each of the s steps; a threshold value may be set based on the s number of reference corrected standardized fluorescence images; while on the other hand an s number of corrected standardized fluorescence images may be calculated by employing the s number of correction functions to perform distance correction to standardized fluorescence images of living tissue; a region for each living tissue of the s steps may be extracted by employing the threshold value on the s number of corrected standardized fluorescence images; and the extracted regions may be displayed superimposed on one another.

Here, s of the aforementioned "s steps" represents a natural number greater than or equal to 2.

The aforementioned "standardized fluorescence images, which are to become reference standardized fluorescence images" refers to standardized fluorescence images imaged and calculated for a sample living tissue of each of the s steps, in order to set the aforementioned threshold value. The aforementioned "corrected standardized images which are to become reference corrected standardized images" refers to images to which distance correction has been administered employing correction functions calculated for each living tissue of the reference standardized fluorescence images.

The aforementioned "standardized fluorescence image of living tissue" refers to the standardized fluorescence image in which living tissue for which actual diagnosis is to be performed is imaged and calculated.

The first standardized image generating apparatus of the present invention comprises: a light emitting means for irradiating living tissue with light; an image detection means for detecting images of mutually different wavelength bandwidths based on reradiated light generated from the living tissue by the irradiation with light; a standardized image generating means for adding a desired offset to at least one of the images of mutually different wavelength bandwidths and generating a standardized image based on the ratio of the images of mutually different wavelength bandwidths, at least one of which a desired offset has been added to; and a correction means for employing a predetermined correction function on the standardized image to perform a distance correction, which corrects for the amount of fluctuation of the standardized image caused by the distance between the living tissue and the image detection means, thereby generating a corrected standardized image.

The second standardized fluorescence image generating apparatus comprises: an excitation light emitting means for irradiating living tissue with excitation light; a fluorescence image detection means for detecting fluorescence images of mutually different wavelength bandwidths based on fluorescent light generated from the living tissue by the irradiation with excitation light; a standardized fluorescence image generating means for adding a desired offset to at least one of the fluorescence images of mutually different wavelength bandwidths and generating a standardized fluorescence image based on the ratio of the fluorescence images of mutually different wavelength bandwidths, at least one of which a desired offset has been added to; and a correction means for employing a predetermined correction function on the standardized image to perform a distance correction, which corrects for the amount of fluctuation of the standardized fluorescence image caused by the distance between the living tissue and the fluorescence image detection means, thereby generating a corrected standardized fluorescence image.

The second standardized image generation apparatus is that wherein the correction means divides the degree of disease progression of a diseased portion of living tissue into s steps; knir and kw are derived for each of the s steps; and the os2 is calculated based on each knir and kw; an s number of corrected standardized fluorescence images, which are to become reference corrected standardized fluorescence images for each living tissue of the s steps, are calculated by employing an s number of correction functions based on the os2 corresponding to each living tissue of s steps to perform distance correction to the standardized fluorescence images for each of the s steps; further comprising: a threshold value setting means for setting a threshold value based on the s number of reference corrected standardized fluorescence images; a region extracting means for extracting a region for each living tissue of s steps by employing the threshold value on the s number of corrected standardized fluorescence images calculated by the correction means employing the s number of correction functions; and a display means for displaying the regions superimposed on one another.

Here, s represents a natural number greater than or equal to 2.

The method and apparatus for standardized image generation of the present invention generates a corrected standardized image by irradiating living tissue with light; detecting images of mutually different wavelength bandwidths based on reradiated light generated from said living tissue by said irradiation with said light with an image detection means; adding a desired offset to at least one of said images of mutually different wavelength bandwidths; and generating a standardized image based on the ratio of said images of mutually different wavelength bandwidths, at least one of which a desired offset has been added to; wherein a predetermined correction function is employed for performing a distance correction on said standardized image, which corrects for the amount of fluctuation of said standardized image caused by the distance between said living tissue and said image detection means. Accordingly, an improvement in the S/N ratio of a calculated standardized value can be obtained by the addition of the offset. Meanwhile, the discrimination of a tissue state of living tissue can be more accurately performed, because a uniform calculated standardized value, which is not dependent on the distance between the image detection means and the living tissue, can be obtained even in a case when this distance changes.

In the case that the aforementioned images of mutually different wavelength bandwidths are a narrow bandwidth fluorescence image and a wide bandwidth fluorescence image, and the aforementioned correction function is calculated based on at least one of the narrow bandwidth fluorescence image and the wide bandwidth fluorescence image, a separate mechanism for deriving the correction function need not be provided; the correction function can be obtained easily, using solely a calculation process.

In the case that the correcting function is calculated based on a reference image obtained by: irradiating a predetermined living tissue, for which a tissue state is known, with a reference light; and detecting a reference image formed of the reflected light reflected by said living tissue with a reference image detection means, the reference image, which is not dependent on the tissue state of the living tissue, reflects just the distance between the living tissue and the reference image detection means, so a distance correction of higher accuracy can be administered.

In the case that the correction function is expressed by Equation (1) below, and the corrected standardized fluorescence image is calculated by Equation (2) below, calculation of the correction function is capable of being performed with an easy calculation process.

$$(nir+os2)/nir \quad \text{Equation 1:}$$

$$\{n/(w+os1)\} \times \{(nir+os2)/nir\} \quad \text{Equation 2:}$$

Here, n is the narrow bandwidth fluorescence image; w is the wide bandwidth fluorescence image; nir is the reference image; os1 is the offset, os2 is the correction coefficient, os2=os1×knir/kw; knir is the reference image divided by the distance between the living tissue and the reference image detection means; and kw is the wide bandwidth fluorescence image divided by the distance between the living tissue and the fluorescence image detection means.

In the case that the degree of disease progression of a diseased portion of living tissue is divided into s steps; knir and kw are derived for each of the s steps; os2 is calculated based on each knir and kw; an s number of corrected standardized fluorescence images, which are to become reference corrected standardized fluorescence images, are calculated by employing an s number of the correction functions based on the os2 corresponding to each living tissue of s steps to perform distance correction to the standardized fluorescence images for each of the s steps; a threshold value is set based on the s number of reference corrected standardized fluorescence images; while on the other hand an s number of corrected standardized fluorescence images are calculated by employing the s number of correction functions to perform distance correction to the standardized fluorescence images of living tissue; a region for each living tissue of the s steps is extracted by employing the threshold value on the s number of corrected standardized fluorescence images; and the extracted regions are displayed superimposed on one another, the degree of disease progression for a living tissue under observation can be more accurately confirmed from the image.

Here, s of the aforementioned "s steps" represents a natural number greater than or equal to 2.

BRIEF DESCRIPTION OF THE DRAWINGS

FIG. 9A and FIG. 9B show images of a single sample based on divided values, wherein FIG. 9A is a case in which the distance between a detection means and living tissue is large, and FIG. 9B is a case in which the distance between a detection means and living tissue is small.

DESCRIPTION OF THE PREFERRED EMBODIMENTS

Figure 1:
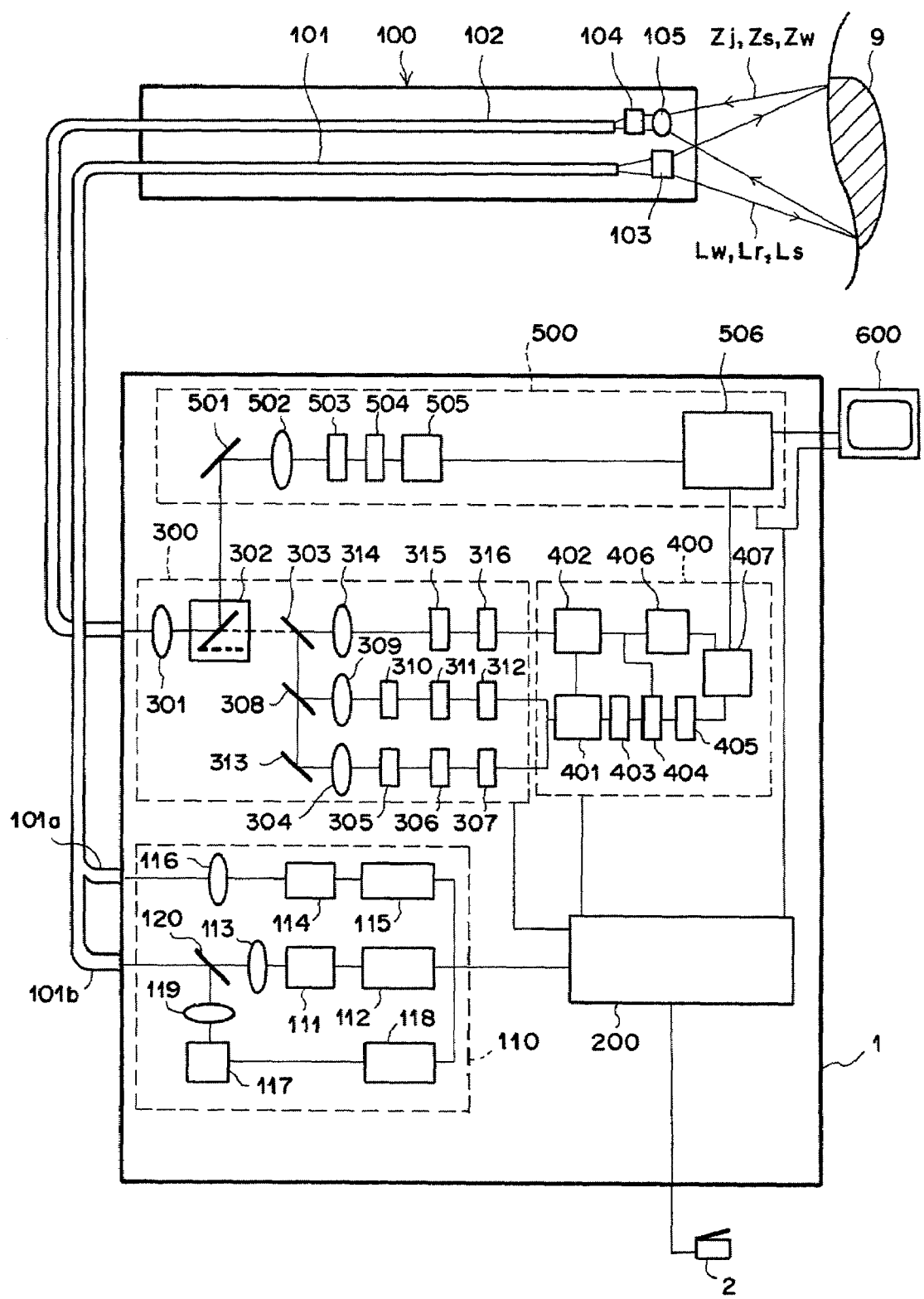
FIG. 1 shows the schematic structure of a fluorescence endoscope that employs a standardized image generation apparatus for carrying out the standardized image generation method according to the first embodiment of the present invention.

Hereinafter, specific embodiments of the present invention will be described with reference to the attached figures. FIG. 1 shows the schematic structure of a fluorescence endoscope that employs a standardized image generation apparatus for carrying out the standardized image generation method according to the first embodiment of the present invention.

The fluorescence endoscope according to the present embodiment comprises: an endoscope insertion portion 100 for insertion into the suspected locus of disease of the patient; an image signal processing portion 1 for processing the data obtained from living tissue by the endoscope insertion portion 100 as image signals; and a monitor 600 for displaying as a visible image the signals processed by the image signal processing portion 1.

The image signal processing portion comprises: an illumination unit 110 equipped with three light sources for emitting a white light Lw for obtaining a standard image, an excitation light Le for obtaining an fluorescence image, and a reference light Lr for obtaining a reference image, respectively; an image detection unit 300 for imaging an fluorescence image Za generated by living tissue 9 due to irradiation thereof by the excitation light Le as well as a reference image Zr generated by the living tissue 9 due to irradiation thereof by the reference light Lr, converting them to digital values and outputting two dimensional image data; an image calculation unit 400 for performing a standardizing calculation on the two dimensional image data of the fluorescence image Za output from the image detection unit 300 then assigning color data to the calculated standardized values, assigning brightness data to the two dimensional image data of the reference image Zr, synthesizing the data of the two images and outputting the synthesized data; a display signal processing unit 500 for converting the standard image to two dimensional image data of digital values, and converting the two dimensional image data as well as the output signal of the image calculation unit 400 to video signals and outputting the video signals; a control computer 200 connected to each of the above units for controlling the operation timings thereof and the like; and a footswitch 2 for switching between a standard image display state and a synthesized image display state (to be described later).

The endoscope insertion portion 100 is equipped with a light guide 101 within its interior which extends to the distal end thereof and an image fiber 102. An illuminating lens 103 is provided at the distal end of the light guide 101, that is, at the distal end of the endoscope insertion portion 100. The image fiber 102 is a multicomponent glass fiber, and has at its distal end an excitation light cutoff filter 104 and a condensing lens 105. A white light light guide 101a, which is a multicomponent glass fiber, and an excitation light light guide 101b, which is a quartz glass fiber are bundled to form the light guide 101 as an integrated cable. The white light light guide 101a and the excitation light light guide 101b are connected to the illumination unit 110. Note that the excitation light light guide 101b also serves as the light guide for guiding reference light. One end of the image fiber 102 is connected to the image detection unit 300.

The illumination unit 110 comprises: a GaN semiconductor laser 111 for emitting excitation light Le for the fluorescence image; a semiconductor laser power source 112 which is electrically connected to the Gan semiconductor laser 111; a white light source 114 for emitting white light Lw for the standard image; a white light power source 115 which is electrically connected to the white light source 114; a reference light source 117 for emitting reference light Lr for the reference image; a reference light power source 118 which is electrically connected to the reference light source 117; and a dichroic mirror 120 that transmits excitation light Le output from the GaN semiconductor laser 111 and perpendicularly reflects reference light Lr output from the reference light source 117.

The image fiber 102 is connected to the image detection unit 300. The image detection unit 300 comprises: a collimating lens 301 for forming the fluorescence image, the standard image, and the reference image propagated by the image fiber 102; a movable mirror 302 for perpendicularly reflecting the standard image transmitted through the collimating lens 301 while transmitting the fluorescence image and the reference image transmitted through the collimating lens 301 by moving to the position indicated by the broken line in the figure; a dichroic mirror 303 for perpendicularly reflecting the fluorescence image (light of wavelengths less than or equal to 750 nm) transmitted through the collimating lens 301; a half mirror 308 for transmitting 50% of the fluorescence image reflected by the dichroic mirror and perpendicularly reflecting the other 50%; a fluorescence image mirror 313 for perpendicularly reflecting the fluorescence image transmitted through the half mirror 308; a wide bandwidth fluorescence image condensing lens 304 for forming the fluorescence image perpendicularly reflected by the fluorescence image mirror 313; a wide bandwidth bandpass filter 305 for selecting wavelengths within the range of 430 nm~730 nm of the fluorescence image transmitted through the wide bandwidth fluorescence image condensing lens 304; a high sensitivity wide bandwidth fluorescence image imaging element 306 for imaging the fluorescence image transmitted through the wide bandwidth bandpass filter 305; an A/D converter 307 for converting the fluorescence image obtained by the high sensitivity wide bandwidth fluorescence image imaging element 306 to digital values and outputting these values as two dimensional image data; a narrow bandwidth fluorescence image condensing lens 309 for forming the fluorescence image perpendicularly reflected by the half mirror 308; a narrow bandwidth bandpass filter 310 for selecting wavelengths within the range of 430 nm~530 nm of the fluorescence image transmitted through the narrow bandwidth fluorescence image condensing lens 309; a high sensitivity narrow bandwidth fluorescence image imaging element 311 for imaging the fluorescence image transmitted through the narrow bandwidth bandpass filter 310; an A/D converter 312 for converting the fluorescence image obtained by the high sensitivity narrow bandwidth fluorescence image imaging element 311 to digital values and outputting these values as two dimensional image data; a reference image condensing lens 314 for forming the reference image transmitted through the dichroic mirror 303; a reference image imaging element 315 for imaging the fluorescence image transmitted through the narrow bandwidth bandpass filter 310; and an A/D converter 316 for converting the reference image obtained by the reference image imaging element 315 to digital values and outputting these values as two dimensional image data.

The image calculation unit 400 comprises: a fluorescence image memory 401 for recording the digitized fluorescence image signal data; a reference image memory 402 for recording the reference image signal data; a standardized fluorescence image generating means 403 for adding a preset offset value to each pixel value of the fluorescence images of the two wavelength bandwidths, then performing a calculation corresponding to the ratios of each of the pixel values to which the offset has been added, thereby calculating a calculated standardized value for each pixel; a correction means 404 for calculating a correction function based on the pixel values of the reference image recorded in the reference image memory 402, then employing the correction function to administer correction on the calculated standardized values output by the standardized fluorescence image generation means 403, thereby calculating a corrected calculated standardized value for each pixel; a color image calculation means 405 for assigning color data to the corrected calculated standardized values calculated by the correction means 404; a brightness image calculation means 406 for assigning brightness data to each pixel value of the reference image recorded in the reference image memory 402; and an image synthesis means 407 for synthesizing the image signal having color data output from the color image calculation means 405 and the image signal having brightness data output from the brightness image calculation means 406, thereby generating and outputting a synthesized image.

The fluorescence image memory 401 is composed of a wide bandwidth fluorescence image memory region and a narrow bandwidth fluorescence image memory region (not shown). The wide bandwidth fluorescence image obtained by the high sensitivity wide bandwidth image imaging element 306 is saved in the wide bandwidth fluorescence image memory region, and the narrow bandwidth fluorescence image obtained by the high sensitivity narrow bandwidth image imaging element 311 is saved in the narrow bandwidth fluorescence image memory region.

The standardized fluorescence image generation means 403 adds an offset value to the pixel values of the fluorescence image recorded in the fluorescence image memory 401, and calculates the ratio between the narrow bandwidth fluorescence image and the wide bandwidth fluorescence image according to Equation (3) below. Note that in the present embodiment, as shown in Equation (3) below, the offset value is added solely to the wide bandwidth fluorescence image. The offset value is a predetermined value recorded in advance in the standardized fluorescence image generation means 403.

$$n/(w+os1) \qquad \text{Equation 3:}$$

Here, n represents the narrow bandwidth fluorescence image, w represents the wide bandwidth fluorescence image, and os1 represents the offset.

The correction means 404 derives the corrected calculated standardized value by multiplying the calculated standardized value calculated by the standardized fluorescence image generation means 403 by a correction function expressed by Equation (1) below. That is, the corrected calculated standardized value is derived according to Equation (2) below. According to the present embodiment, the correction function is calculated from the reference image, as shown in Equation (1) below. The correction means 404 calculates the correction function from the pixel values of the reference image recorded in the reference image memory 402. In addition, os2 is calculated according to Equation (4) below, wherein knir is the reference image divided by the distance between living tissue 9 and the distal end of the endoscope insertion portion 100, and kw is the wide bandwidth fluorescence image divided by the distance between the living tissue 9 and the distal end of the endoscope insertion portion 100.

$$(nir+os2)/nir \qquad \text{Equation 1:}$$

Here, nir represents the reference image, and os2 represents the correction coefficient.

$$\{n/(w+os1)\} \times \{(nir+os2)/nir\} \qquad \text{Equation 2:}$$

$$os2 = os1 \times knir/kw \qquad \text{Equation 4:}$$

Here, knir represents the reference image divided by the distance between the distal end of the endoscope insertion portion 100 and the living tissue 9, and kw represents the wide bandwidth fluorescence image divided by the distance between the distal end of the endoscope insertion portion 100 and the living tissue 9.

The color image calculation means 405 generates a color image by assigning color data to the corrected pixel values calculated by the correction means 404 according to the sizes thereof.

The brightness image calculation means 406 generates a brightness image by assigning brightness data to the pixel values recorded in the reference image memory 402 according to the sizes thereof.

The image synthesis means 407 synthesizes the color image output by the color image calculation means 405 and the brightness image output by the brightness image calculation means 406, and outputs the synthesized image to a video signal processing circuit 506 of the display signal processing unit 500, to be described below.

The display signal processing unit 500 comprises: a standard image mirror 501 for perpendicularly reflecting the standard image reflected by the movable mirror 302; a standard image condensing lens 502 for forming the standard image reflected by the standard image mirror; a standard image imaging element 503 for obtaining the image formed by the standard image condensing lens 502; an A/D converter 504 for converting the standard image obtained by the standard image imaging element 503 to digital values and outputting the digital values as two dimensional image data; a standard image memory 505 for recording the digitized standard image signal; and a video signal processing circuit 506 for converting the standard image signal output from the standard image memory 505 and the synthesized image signal output from the image synthesis means 407 to a video signal and outputting the video signal. A monitor 600 is provided that switches between display of the standard image and the synthesized image.

Next, the operation of the fluorescence endoscope according to the present embodiment will be described. First, the operation in the case that fluorescence images of mutually different wavelength bandwidths and a reference image are obtained, and a synthesized image is generated therefrom and displayed will be described.

When the synthesized image is to be displayed, excitation light Le is emitted from the GaN semiconductor laser 111 by the driving of the semiconductor laser power source 112 based on a signal from the control computer 200. The excitation light Le is transmitted through the excitation light condensing lens 113, transmitted through the dichroic mirror 120, enters the excitation light light guide 101b, and after being guided to the distal end of the endoscope insertion portion 100, is irradiated onto living tissue 9 from the illuminating lens 103. The fluorescence image generated from living tissue 9 by the irradiation thereof by excitation light Le is condensed by the condensing lens 105, is transmitted through the excitation light cutoff filter 104, enters the tip of the image fiber 102, and enters the collimating lens 301 via the image fiber 102. The excitation light cutoff filter 104 is a long pass filter that transmits all fluorescence having wavelengths greater than or equal to 420 nm. Because the wavelength of the excitation light Le is 410 nm, the excitation light reflected by living tissue 9 is cutoff by the excitation light cutoff filter 104. The fluorescence image transmitted through the collimating lens 301 is perpendicularly reflected by the dichroic mirror. Then, the fluorescence image is transmitted at a 50% transmittance rate and reflected at a 50% reflectance rate by the half mirror 308. The fluorescence image transmitted through the half mirror 308 is perpendicularly reflected by the fluorescence image mirror 313 and formed by the wide bandwidth fluorescence image condensing lens 304. The fluorescence image formed by the fluorescence image condensing lens 304 is transmitted through the wide bandwidth bandpass filter 305 and is obtained by the high sensitivity wide bandwidth fluorescence image imaging element 306. The image signal from the high sensitivity wide bandwidth fluorescence image imaging element 306 is input into the A/D converter 307, digitized thereby, then saved in the wide bandwidth fluorescence image memory region of the fluorescence image memory 401.

The fluorescence image reflected by the dichroic mirror 303 and reflected by the half mirror 308 is formed by the narrow bandwidth fluorescence image condensing lens 309, transmitted through the narrow bandwidth bandpass filter 310, and obtained by the high sensitivity narrow bandwidth fluorescence image imaging element 311. The image signal from the high sensitivity narrow bandwidth fluorescence image imaging element 311 is input into the A/D converter 312, digitized thereby, then saved in the narrow bandwidth fluorescence image memory region of the fluorescence image memory 401. Note that the digital data representing the fluorescence image obtained by the high sensitivity wide bandwidth fluorescence image imaging element 306 and the digital data representing the fluorescence image obtained by the high sensitivity narrow bandwidth fluorescence image imaging element 311 are saved in mutually different regions of the fluorescence image memory 401. Note also that at this time, the movable mirror 302 is in the position indicated by the broken line in the figure, parallel to the optical axis of the fluorescence image.

In addition, reference light Lr is emitted from the reference light source 117 by driving of the reference light power source 118. The reference light Lr is transmitted through the reference light condensing lens 119, perpendicularly reflected by the dichroic mirror 120, enters the excitation light light guide 101b, and after being guided to the distal end of the endoscope insertion portion 100, is irradiated onto living tissue 9 from the illuminating lens 103. The reference image generated from living tissue 9 by the irradiation thereof with the reference light Lr is condensed by the condensing lens 105, is transmitted through the excitation light cutoff filter 104, enters the tip of the image fiber 102, and enters the collimating lens 301 via the image fiber 102. The excitation light cutoff filter is a long pass filter that transmits the reference image, which has wavelengths greater than or equal to 420 nm. The reference image transmitted through the collimating lens is transmitted through the dichroic mirror 303, formed by the reference image condensing lens, and obtained by the reference image imaging element 315. The image signal from the reference image imaging element is input into the A/D converter 316, digitized thereby, then saved in the reference image memory 402. Note that at this time, the movable mirror 302 is in the position indicated by the broken line in the figure, parallel to the optical axis of the reference image.

Of the fluorescence images of two bandwidths saved in the fluorescence image memory 401, the offset os1 is added only to each pixel value of the wide bandwidth fluorescence image by the standardized fluorescence image generation means 403. Then, the ratio thereto of the narrow bandwidth fluorescence image is calculated according to Equation 3 below. Note that os1 is a predetermined value set in advance in the standardized fluorescence image generation means 403.

$$n/(w+os1) \qquad \text{Equation 3:}$$

Here, n represents the narrow bandwidth fluorescence image, w represents the wide bandwidth fluorescence image, and os1 represents the offset.

Then, the calculated standardized value calculated by the standardized fluorescence image generation means 403 is output to the correction means 404, and a corrected calculated standardized value is calculated according to Equation 2 below by the correction means 403.

$$\{n/(w+os1)\} \times \{(nir+os2)/nir\} \qquad \text{Equation 2:}$$

$$os2 = os1 \times knir/kw$$

Here, nir represents the reference image; os2 represents the correction coefficient; knir represents the reference image divided by the distance between the distal end of the endoscope insertion portion 100 and the living tissue 9, and kw represents the wide bandwidth fluorescence image divided by the distance between the distal end of the endoscope insertion portion 100 and the living tissue 9.

Figure 2:
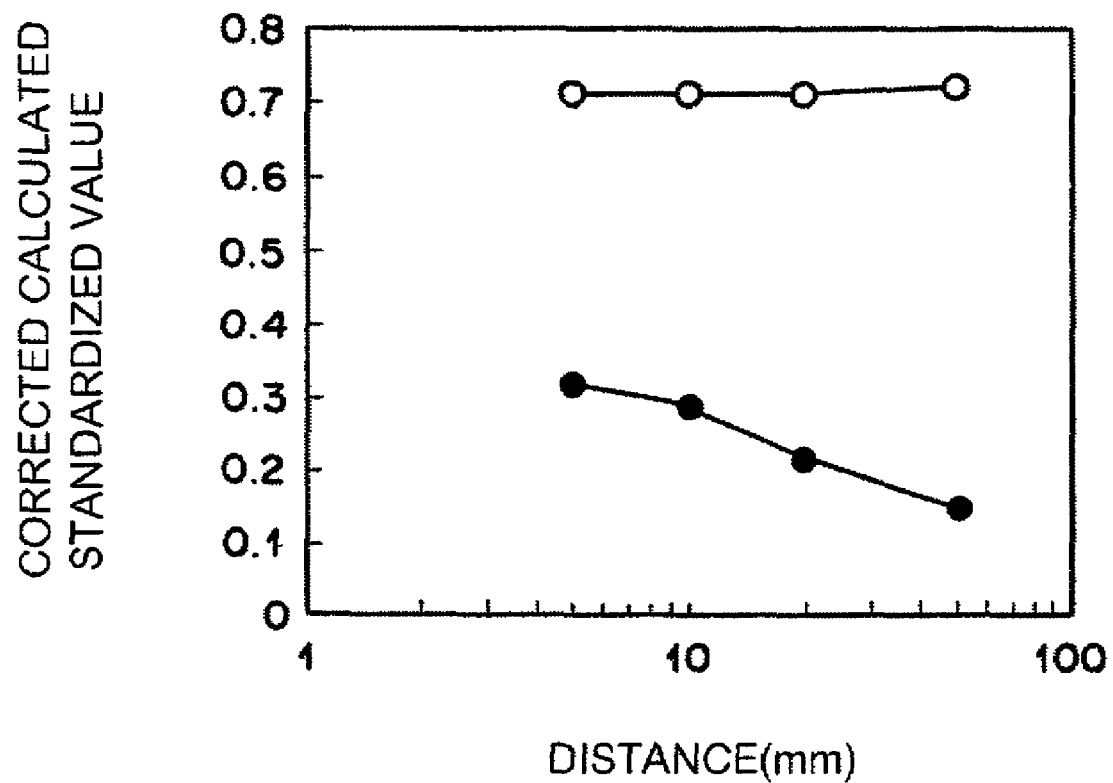
FIG. 2 shows a graph illustrating the relationship between corrected calculated standardized values and distances between the distal end of an endoscope insertion portion 100 and living tissue 9, for a case in which fluorescence images and a reference image are obtained of living tissue having normal portions and diseased portions.

Note that the correction function (nir+os2)/nir is a value which has been calculated in advance using a reference image and a wide bandwidth fluorescence image of a predetermined living tissue detected by the fluorescence endoscope according to the present embodiment, and has been recorded in the correction means 404 in advance. According to the present embodiment, a normal tissue is employed as the aforementioned predetermined living tissue of which a reference image and a wide bandwidth fluorescence image is obtained to calculate the aforementioned correction function. FIG. 2 shows a graph illustrating the relationship between the corrected calculated standardized values and the distances between the distal end of the endoscope insertion portion 100 and living tissue 9, for a case in which fluorescence images and a reference image are obtained of living tissue actually having normal portions and diseased portions, after setting the correction function in advance as described above. With regard to the graph of FIG. 2, the outlined circles indicate the corrected calculated standardized values for the normal portions of living tissue, and the solid circles indicate the corrected calculated standardized values for the diseased portions of living tissue. According to the present embodiment, because the correction function has been calculated based on normal tissue as described above, the corrected calculated standardized values for the normal portions of living tissue have a substantially uniform value independent of the distance, as shown in the figure. Accordingly, a threshold value may be derived based on, for example, the corrected calculated standardized values indicated by the outlined circles, and living tissue corresponding to corrected standardized values greater than or equal to this threshold value may be judged to be normal, while living tissue corresponding to corrected calculated standardized values less than this threshold value may be judged to be diseased. The threshold value may be set, for example, by deriving a plurality of mean values (for a plurality of patients) of the corrected calculated standardized values indicated by the outlined circles, that is, for normal tissue, deriving the standard deviation σ thereof, and setting the threshold value as the mean value–2σ or the mean value–3σ. Whether to subtract 2σ or 3σ from the mean value can be determined by the relationship between the corrected calculated standardized values of diseased tissue and those of normal tissue.

Instead of calculating the correction function based on normal tissue as in the present embodiment, the correction function may alternatively be calculated based on diseased tissue. In this case, the corrected calculated standardized values for the diseased portions of living tissue will have a substantially uniform value independent of the distance. Accordingly, a threshold value may be derived based on these corrected calculated standardized values in a similar manner as described above, and living tissue corresponding to corrected standardized values greater than this threshold value may be judged to be normal, while living tissue corresponding to corrected calculated standardized values less than this threshold value may be judged to be diseased. The threshold value may be set, for example, by deriving a plurality of mean values (for a plurality of patients) of the corrected calculated standardized values for diseased tissue, deriving the standard deviation o thereof, and setting the threshold value as the mean value+2σ or the mean value+3σ.

Then, color data is assigned to each pixel of the corrected standardized image, based on the Boolean judgment made with regard to the corrected calculated standardized values as described above, by the color image calculation means 405. The color image calculation means 405 outputs a color image signal obtained thereby to the image synthesis means 407. Meanwhile, the brightness image calculation means 406 assigns brightness data to each pixel of the reference image saved in the reference image memory 402, and outputs a brightness image signal obtained thereby. The two image signals output by the color image calculation means 405 and the brightness image calculation means 406, respectively, are synthesized by the image synthesis means 407.

The synthesized image synthesized by the image synthesis means 407 are D/A converted by the video signal processing circuit 506, then input to the monitor 600, thereby displaying the synthesized image.

Next the operation in the case that a standard image is displayed will be described. First, white light Lw is emitted from the white light source 114 by the driving of the white light power source 115 based on a signal from the control computer 200. The white light Lw enters the white light light guide 101a via the white light condensing lens 116, guided to the distal end of the endoscope insertion portion 100, then irradiated onto living tissue 9 from the illumination lens 103. The reflected light of the white light Lw is condensed by the condensing lens 105, is transmitted through the excitation light cutoff filter 104, enters the tip of the image fiber 102, and enters the collimating lens 301 via the image fiber 102. The excitation light cutoff filter is a long pass filter that transmits visible light, which has wavelengths greater than or equal to 420 nm. The reflected light transmitted through the collimating lens 301 is reflected by the movable mirror 302 as well as the standard image mirror 501, and enters the standard image condensing lens 502. The standard image condensed by the standard image condensing lens 502 is formed on the standard image imaging element 503, and obtained thereby. The image signal from the standard image imaging element 503 is input into the A/D converter 504, digitized thereby, then saved in the standard image memory 505. The standard image saved in the standard image memory 505 is D/A converted, then input to the monitor 600, and displayed thereon as a visible image.

The series of operations relating to the display of the aforementioned synthesized image as well as the display of the standard image is controlled by the control computer 200.

According to the aforementioned embodiment, in which the standardized image generation method and apparatus of the present invention has been applied, the aforementioned correction function is employed for performing a distance correction on a standardized fluorescence image (calculated standardized value), which corrects for the amount of fluctuation of the standardized fluorescence image (calculated standardized value) caused by the distance between living tissue 9 and the distal end of the endoscope insertion portion 100 to generate a corrected standardized fluorescence image (corrected calculated standardized value). Accordingly, an improvement in the S/N ratio of a standardized fluorescence image (calculated standardized value) can be obtained by the addition of the offset. Meanwhile, the discrimination between images of normal tissue and diseased tissue can be more accurately performed, because a uniform calculated standardized value, which is not dependent on the distance between the distal end of the endoscope insertion portion 100 and the living tissue 9, can be obtained even in a case when this distance changes.

Figure 3A:
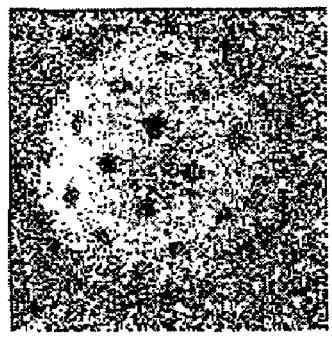
FIG. 3A and FIG. 3B show images on which distance correction has been administered for the far image and the close image of a single sample shown in FIG. 9A and FIG. 9B.
Figure 3B:
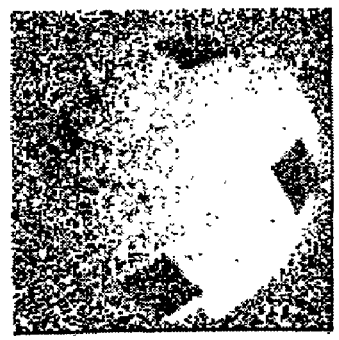
Figure 9A:
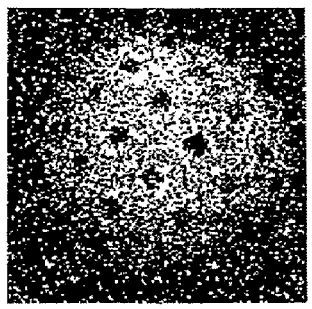
Figure 9B:
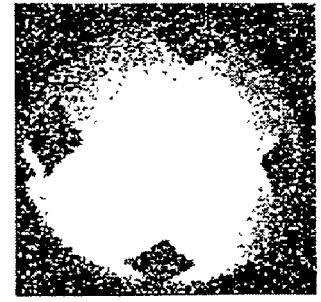
Figure 10:
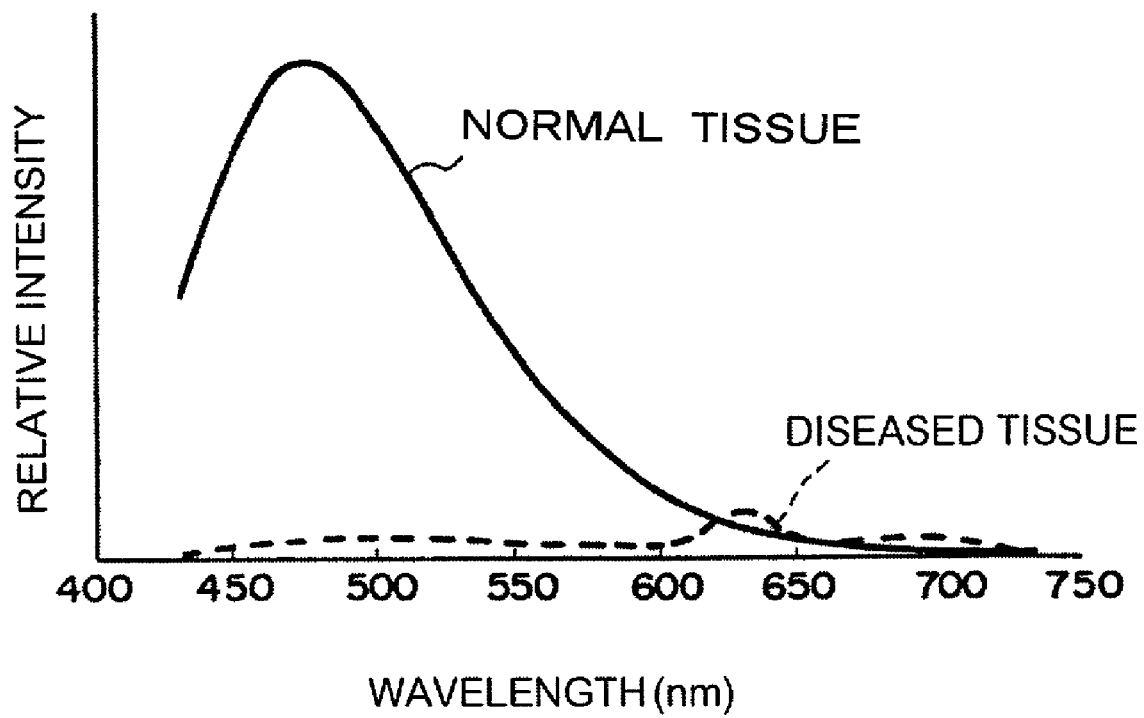
FIG. 10 is a graph that shows the intensity distribution of fluorescence spectra for normal and diseased tissue.

For example, FIG. 3A and FIG. 3B show images on which the aforementioned distance correction has been administered for the far image and the close image of a single sample shown in FIG. 9A and FIG. 9B. Note that the images of FIG. 3A and FIG. 3B are not those in which the results of a Boolean judgment have been displayed as in the above embodiment, but rather those in which brightness data has been assigned corresponding to the size of the corrected calculated standardized value, displayed as brightness images. It is apparent from the figures that, when compared to FIG. 9A and FIG. 9B, the difference in the brightness of the normal portions, as well as the difference in contrast between the normal and diseased portions are smaller between the far image (FIG. 3A) and the close image (FIG. 3B).

Further, a method wherein the corrected calculated standardized value is calculated employing a correction function based on the reference image according to Equation (1) and Equation (3) has been described in the first embodiment above. However, an alternate method of calculating the corrected calculated standardized value employing a correction function derived based on the reference image will be described below.

First, a narrow bandwidth fluorescence image, a wide bandwidth fluorescence image, and a reference image of a normal portion of living tissue is obtained in order to derive a correction function, in a similar manner to that of the embodiment described above. The pixel values of each image are recorded in the fluorescence image memory 401 and the reference image memory 402. Next, the offset os1 is added solely to the wide bandwidth fluorescence image, of the fluorescence images of two wavelength bandwidths saved in the fluorescence image memory 401, by the standardized fluorescence image generation means 403. Then, the ratio thereto of the narrow bandwidth fluorescence image is calculated according to Equation 3 below. Note that os1 is a predetermined value set in advance in the standardized fluorescence image generation means 403.

$$n/(w+os1) \qquad \text{Equation 3:}$$

Here, n represents the narrow bandwidth fluorescence image, w represents the wide bandwidth fluorescence image, and os1 represents the offset.

Figure 4A:
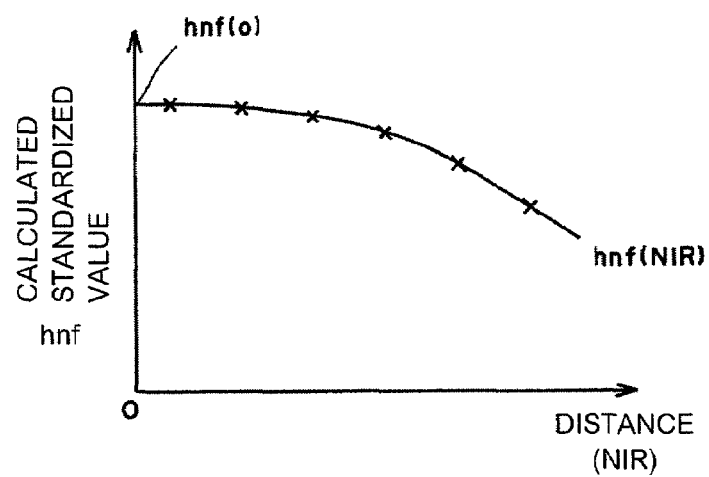
FIG. 4A is a graph that shows the relationship between calculated standardized values based on a narrow bandwidth fluorescence image and a wide bandwidth fluorescence image and NIR, which is the inverse of the pixel values of a reference image.

The calculated standardized value calculated by the standardized fluorescence image generation means 403 is output to the correction means 404. Meanwhile, the pixel values of the reference image saved in the reference image memory 402 are output to the correction means 404. The correction means 404 derives and records a correction function hnf (NIR) as indicated in FIG. 4A based on the calculated standardized values output from the standardized fluorescence image generation means 403 and the pixel values of the reference image output from the reference image memory 402. Here, hnf represents a function based on the square of the inverse of the pixel values of the reference image obtained at this time. NIR, the distance between the distal end of the endoscope insertion portion 100 and the living tissue, is the variable in this function. Note that the distance NIR is calculated from the aforementioned square of the inverse of the pixel values of the reference image. The reference image is that which is obtained from reflected light of irradiated reference light, which is substantially unabsorbed by living tissue. Therefore, the sizes of the pixel values thereof are dependent on the distance between the distal end of the endoscope insertion portion 100 and the living tissue. Accordingly, the function hnf, which is based on the square of the inverse of the pixel values of the reference image, can be said to directly reflect the aforementioned distance.

When living tissue which is the actual target tissue for diagnosis is imaged, calculated standardized values are calculated for the narrow bandwidth fluorescence image and the wide bandwidth fluorescence image thereof according to Equation 3 above. Then, these calculated standardized values as well as the pixel values of the reference image are output to the correction means 404, and a corrected calculated standardized value is output according to Equation 5 below.

$$nf \times hnf(0)/hnf(NIR) \qquad \text{Equation 5:}$$

Here, nf represents the calculated standardized value based on the imaged fluorescence images.

Figure 4B:
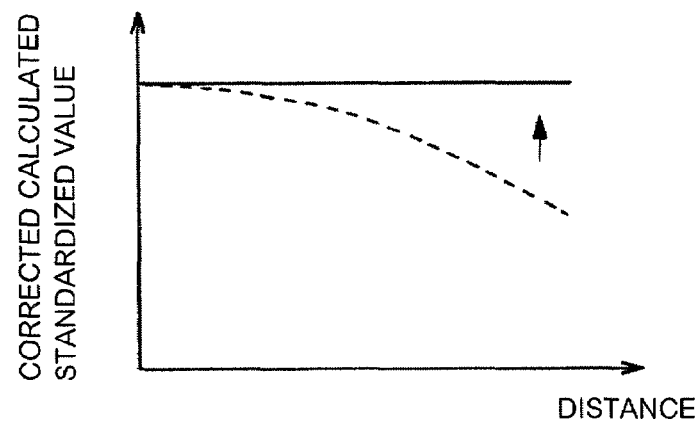
FIG. 4B is a graph that shows the relationship between calculated standardized values based on a narrow bandwidth fluorescence image and a wide bandwidth fluorescence image, corrected by a correction function, and NIR, which is the inverse of the pixel values of a reference image.

By deriving the corrected calculated standardized value by employing a correction function as described above, the actual calculated standardized value (indicated by the broken line in FIG. 4B) which is dependent on distance may be corrected to the corrected calculated standardized value (indicated by the solid line in FIG. 4B) which is independent of distance. The operations occurring after this corrected calculated standardized value is calculated are the same as those described in the first embodiment above.

Figure 5:
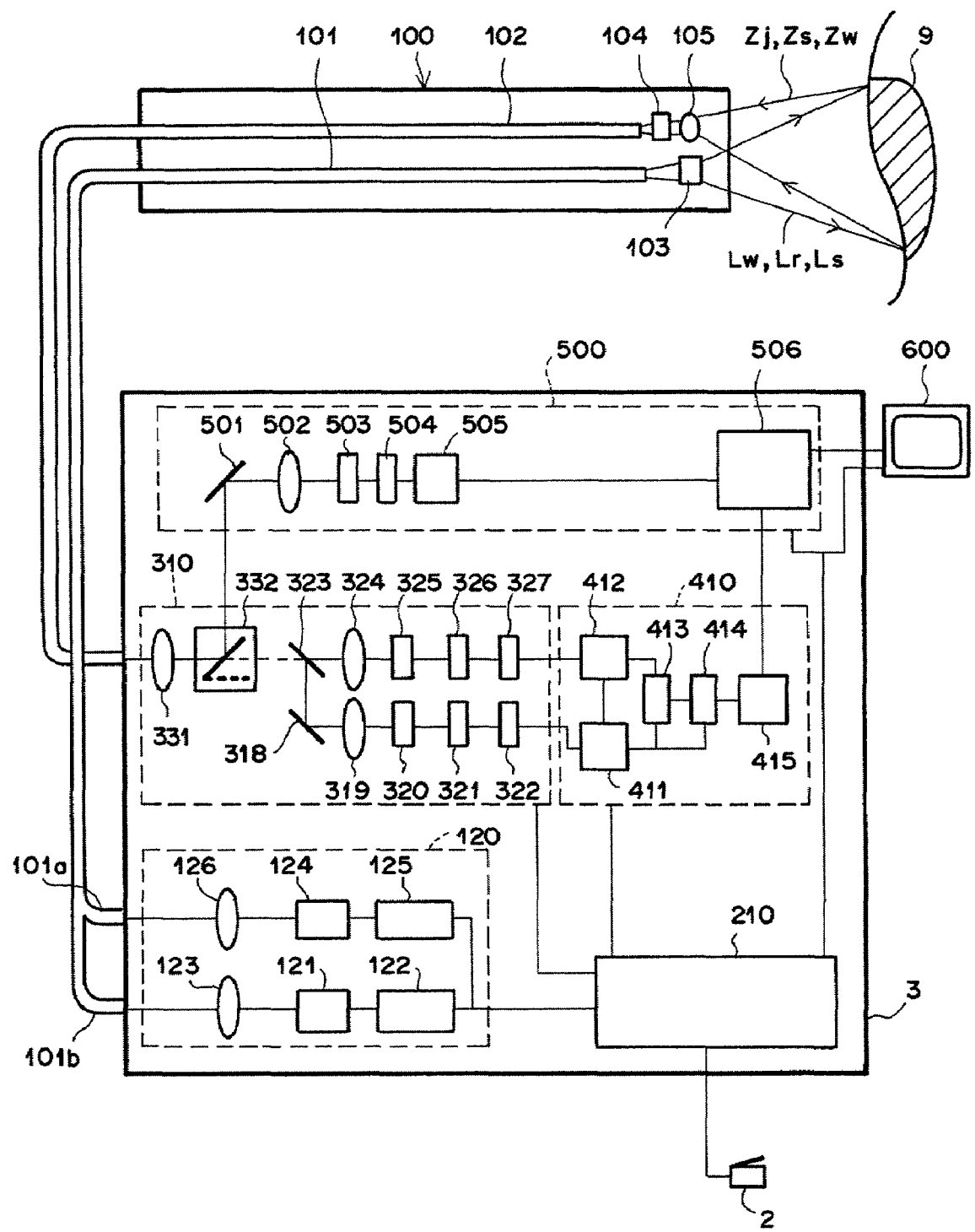
FIG. 5 shows the schematic structure of a fluorescence endoscope that employs a standardized image generation apparatus for carrying out the standardized image generation method according to the second embodiment of the present invention.

Next, a fluorescence endoscope that employs a standardized image generation apparatus for carrying out the standardized image generation method according to the second embodiment of the present invention will be described. FIG. 5 shows the schematic structure of the second embodiment. Note that with regard to the second embodiment, elements which are the same as those in the first embodiment have been labeled with the same reference numerals, and unless particularly necessary, descriptions thereof are omitted.

The fluorescence endoscope according to the present embodiment differs from the first embodiment by being of a configuration which does not utilize reference light.

The image signal processing portion comprises: an illumination unit 120 equipped with two light sources for emitting a white light Lw for obtaining a standard image, and an excitation light Le for obtaining an fluorescence image, respectively; an image detection unit 310 for imaging an fluorescence image Za generated by living tissue 9 due to irradiation thereof by the excitation light Le, converting them to digital values and outputting two dimensional image data; an image calculation unit 410 for performing a standardizing calculation on the two dimensional image data of the fluorescence image Za output from the image detection unit 300 then assigning color data to the calculated standardized values; a display signal processing unit 500 for converting the standard image to two dimensional image data of digital values, and converting the two dimensional image data as well as the output signal of the image calculation unit 410 to video signals and outputting the video signals; a control computer 210 connected to each of the above units for controlling the operation timings thereof and the like; and a footswitch 2 for switching between a standard image display state and a color image display state (to be described later).

The illumination unit 120 comprises: a GaN semiconductor laser 121 for emitting excitation light Le for the fluorescence image; a semiconductor laser power source 122 which is electrically connected to the Gan semiconductor laser 121; a white light source 124 for emitting white light Lw for the standard image; and a white light power source 125 which is electrically connected to the white light source 124.

The image fiber 102 is connected to the image detection unit 310. The image detection unit 300 comprises: a collimating lens 331 for forming the fluorescence image and the standard image propagated by the image fiber 102; a movable mirror 332 for perpendicularly reflecting the standard image transmitted through the collimating lens 331 while transmitting the fluorescence image transmitted through the collimating lens 331 by moving to the position indicated by the broken line in the figure; a half mirror 323 for transmitting 50% of the fluorescence image (light of wavelengths less than or equal to 750 nm) transmitted through the collimating lens 331 and perpendicularly reflecting the other 50%; a narrow bandwidth fluorescence image condensing lens 324 for forming the fluorescence image perpendicularly transmitted through the half mirror 323; a narrow bandwidth bandpass filter 325 for selecting wavelengths within the range of 430 nm~530 nm of the fluorescence image transmitted through the narrow bandwidth fluorescence image condensing lens 324; a high sensitivity narrow bandwidth fluorescence image imaging element 326 for imaging the fluorescence image transmitted through the narrow bandwidth bandpass filter 325; an A/D converter 327 for converting the fluorescence image obtained by the high sensitivity narrow bandwidth fluorescence image imaging element 326 to digital values and outputting these values as two dimensional image data; a fluorescence image mirror 318 for perpendicularly reflecting the fluorescence image perpendicularly reflected by the half mirror 323; a wide bandwidth fluorescence image condensing lens 319 for forming the fluorescence image perpendicularly reflected by the fluorescence image mirror 318; a wide bandwidth bandpass filter 320 for selecting wavelengths within the range of 430 nm~730 nm of the fluorescence image transmitted through the wide bandwidth fluorescence image condensing lens 319; a high sensitivity wide bandwidth fluorescence image imaging element 321 for imaging the fluorescence image transmitted through the wide bandwidth bandpass filter 320; and an A/D converter 322 for converting the fluorescence image obtained by the high sensitivity wide bandwidth fluorescence image imaging element 321 to digital values and outputting these values as two dimensional image data.

The image calculation unit 410 comprises: a wide bandwidth fluorescence image memory 411 for recording the digitized wide bandwidth fluorescence image signal data; a narrow bandwidth fluorescence image memory 412 for recording the digitized narrow bandwidth fluorescence image signal data; a standardized fluorescence image generating means 413 for adding a preset offset value to each pixel value of the wide bandwidth fluorescence image recorded in the wide bandwidth fluorescence image memory 411, then performing a calculation corresponding to the ratios to the pixel values to which the offset has been added of the pixel values of the narrow bandwidth fluorescence image, thereby calculating a calculated standardized value for each pixel; a correction means 414 for calculating a correction function based on the pixel values of the wide bandwidth fluorescence image recorded in the wide bandwidth fluorescence image memory 411, then employing the correction function to administer correction on the calculated standardized values output by the standardized fluorescence image generation means 413, thereby calculating a corrected calculated standardized value for each pixel; and a color image calculation means 415 for assigning color data to the corrected calculated standardized values calculated by the correction means 414.

The standardized fluorescence image generation means 413 adds an offset value to the pixel values of the wide bandwidth fluorescence image recorded in the wide bandwidth fluorescence image memory 411, and calculates the ratio thereto of the narrow bandwidth fluorescence image and the wide bandwidth fluorescence according to Equation (3) below. Note that the offset value is a predetermined value recorded in advance in the standardized fluorescence image generation means 413.

$n/(w+os1)$ Equation 3:

Here, n represents the narrow bandwidth fluorescence image, w represents the wide bandwidth fluorescence image, and os1 represents the offset.

The correction means 414 administers distance correction on the calculated standardized values by employing a correction function derived from the pixel values of the wide bandwidth fluorescence image and the calculated standardized values calculated by the standardized fluorescence image generation means, and outputs corrected calculated standardized values. The details of this operation will be described later.

The color image calculation means 415 assigns color data according to the size of the corrected pixel values calculated by the correction means 414, thereby generating a color image.

Next, the operation of the fluorescence endoscope according to the present embodiment will be described. First, the operation in the case that fluorescence images of two mutually different wavelength bandwidths are obtained, and a color image is generated therefrom and displayed will be described.

When the color image is to be displayed, excitation light Le is emitted from the GaN semiconductor laser 121 by the driving of the semiconductor laser power source 122 based on a signal from the control computer 210. The excitation light Le is transmitted through the excitation light condensing lens 123, enters the excitation light light guide 101b, and after being guided to the distal end of the endoscope insertion portion 100, is irradiated onto living tissue 9 from the illuminating lens 103. The fluorescence image generated from living tissue 9 by the irradiation thereof by excitation light Le is condensed by the condensing lens 105, is transmitted through the excitation light cutoff filter 104, enters the tip of the image fiber 102, and enters the collimating lens 331 via the image fiber 102. The excitation light cutoff filter 104 is a long pass filter that transmits all fluorescence having wavelengths greater than or equal to 420 nm. Because the wavelength of the excitation light Le is 410 nm, the excitation light reflected by living tissue 9 is cutoff by the excitation light cutoff filter 104. The fluorescence image transmitted through the collimating lens 331 is transmitted at a 50% transmittance rate and reflected at a 50% reflectance rate by the half mirror 313. The fluorescence image reflected by the half mirror 313 is perpendicularly reflected by the fluorescence image mirror 318 and formed by the wide bandwidth fluorescence image condensing lens 319. The fluorescence image formed by the fluorescence image condensing lens 319 is transmitted through the wide bandwidth bandpass filter 320 and is obtained by the high sensitivity wide bandwidth fluorescence image imaging element 321. The image signal from the high sensitivity wide bandwidth fluorescence image imaging element 321 is input into the A/D converter 322, digitized thereby, then saved in the wide bandwidth fluorescence image memory 411.

The fluorescence image transmitted through the half mirror 313 is formed by the narrow bandwidth fluorescence image condensing lens 314, transmitted through the narrow bandwidth bandpass filter 315, and obtained by the high sensitivity narrow bandwidth fluorescence image imaging element 316. The image signal from the high sensitivity narrow bandwidth fluorescence image imaging element 316 is input into the A/D converter 317, digitized thereby, then saved in the narrow bandwidth fluorescence image memory 412. Note that the digital data representing the fluorescence image obtained by the high sensitivity wide bandwidth fluorescence image imaging element 321 and the digital data representing the fluorescence image obtained by the high sensitivity narrow bandwidth fluorescence image imaging element 316 may each be saved in mutually different regions of a common memory. Note also that at this time, the movable mirror 332 is in the position indicated by the broken line in the figure, parallel to the optical axis of the fluorescence image.

In a similar manner to the previous embodiment, a narrow bandwidth fluorescence image and a wide bandwidth fluorescence image is obtained for a normal portion of living tissue in order to derive the correction function in the present embodiment. The pixel values of each of the obtained fluorescence images are recorded in the wide bandwidth fluorescence image memory 411 and the narrow bandwidth fluorescence image memory 412. The offset os1 is added to each pixel value of the wide bandwidth fluorescence image saved in the wide bandwidth fluorescence image memory 411 by the standardized fluorescence image generation means 413. Then, the ratio thereto of the narrow bandwidth fluorescence image is calculated according to Equation 3 below. Note that os1 is a predetermined value set in advance in the standardized fluorescence image generation means 413.

$$n/(w+os1) \quad \text{Equation 3:}$$

Here, n represents the narrow bandwidth fluorescence image, w represents the wide bandwidth fluorescence image, and os1 represents the offset.

Figure 6A:
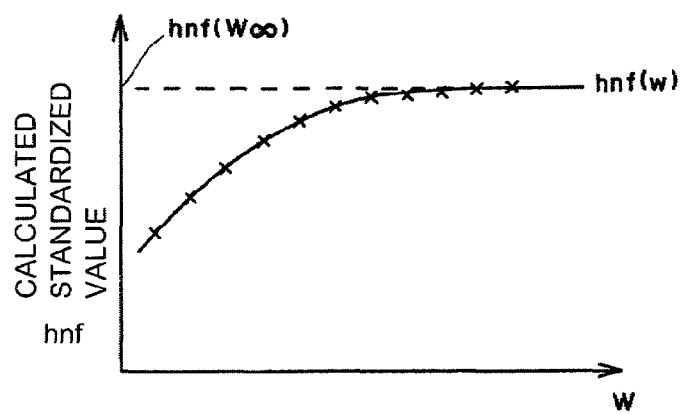
FIG. 6A is a graph that shows the relationship between calculated standardized values based on a narrow bandwidth fluorescence image and a wide bandwidth fluorescence image and the pixel values of a wide bandwidth fluorescence image.

Then, the calculated standardized value calculated by the standardized fluorescence image generation means 413 is output to the correction means 414. Meanwhile, the pixel values of the wide bandwidth fluorescence image recorded in the wide bandwidth fluorescence image memory 411 are also output to the correction means 414. The correction means 414 derives and records a correction function hnf(w) like that shown in FIG. 6a based on the calculated standardized value calculated by the standardized fluorescence image generation means 413 and the pixel values of the wide bandwidth fluorescence image recorded in the wide bandwidth fluorescence image memory 411. Here, w represents the pixel values of the obtained wide bandwidth fluorescence image. Note that $w_\infty$ represents the size of the pixel value of the wide bandwidth fluorescence image in the case that the distance between the distal end of the endoscope insertion portion and the living tissue is substantially 0 (extremely close), and it is a sufficiently large value.

When living tissue which is the actual target tissue for diagnosis is imaged, calculated standardized values are calculated for the narrow bandwidth fluorescence image and the wide bandwidth fluorescence image thereof according to Equation 3 above. Then, these calculated standardized values as well as the pixel values of the wide bandwidth fluorescence image are output to the correction means 414, and a corrected calculated standardized value is output according to Equation 6 below.

$$nf \times hnf(w_\infty)/hnf(w) \quad \text{Equation 6:}$$

Here, nf represents the calculated standardized value based on the imaged fluorescence images, and hnf (w) represents the value of the correction function hnf(w) for pixel values w of the obtained wide bandwidth fluorescence image.

Figure 6B:
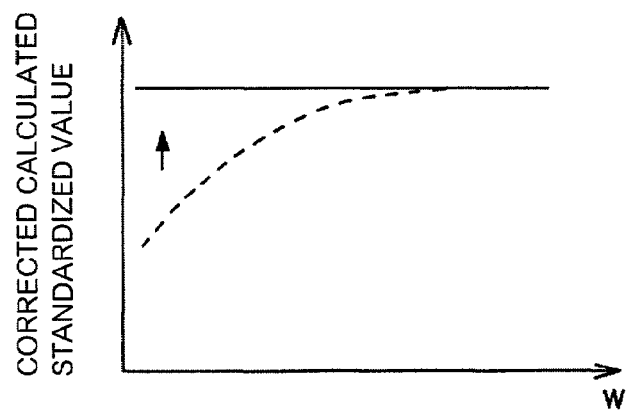
FIG. 6B is a graph that shows the relationship between calculated standardized values based on a narrow bandwidth fluorescence image and a wide bandwidth fluorescence image, corrected by a correction function, and the pixel values of a wide bandwidth fluorescence image.

By deriving the corrected calculated standardized value by employing a correction function as described above, the actual calculated standardized value (indicated by the broken line in FIG. 6B) which is dependent on distance may be corrected to the corrected calculated standardized value (indicated by the solid line in FIG. 6B) which is independent of distance.

According to the present embodiment, because the correction function has been calculated based on normal tissue as described above, a threshold value may be derived based on the corrected calculated standardized values in the same manner as that of the first embodiment, and living tissue corresponding to corrected standardized values greater than or equal to this threshold value may be judged to be normal, while living tissue corresponding to corrected calculated standardized values less than this threshold value may be judged to be diseased. The threshold value may be set in the same manner as that of the first embodiment. In addition, the manner of deriving the threshold value in the case that the correction function is calculated based on diseased tissue is the same as that of the first embodiment.

Then, color data is assigned to each pixel of the corrected standardized image, based on the Boolean judgment made with regard to the corrected calculated standardized values as described above, by the color image calculation means 415. The color image signal is D/A converted by the video signal processing circuit 506, then input to the monitor 600, thereby displaying the color image. The other operations are performed in the same manner as that of the first embodiment.

Further, with regard to the second embodiment, the correction function was derived from the relationship between the calculated standardized values based on the fluorescence images and the pixel values of wide bandwidth fluorescence image. However, the derivation of the correction function is not limited to this method. The correction function may alternatively be derived from the relationship between the pixel values of the narrow band fluorescence image and the calculated standardized values, or the relationship between the sums of the pixel values of the narrow bandwidth fluorescence image and the wide bandwidth fluorescence image and the calculated standardized values.

Figure 7:
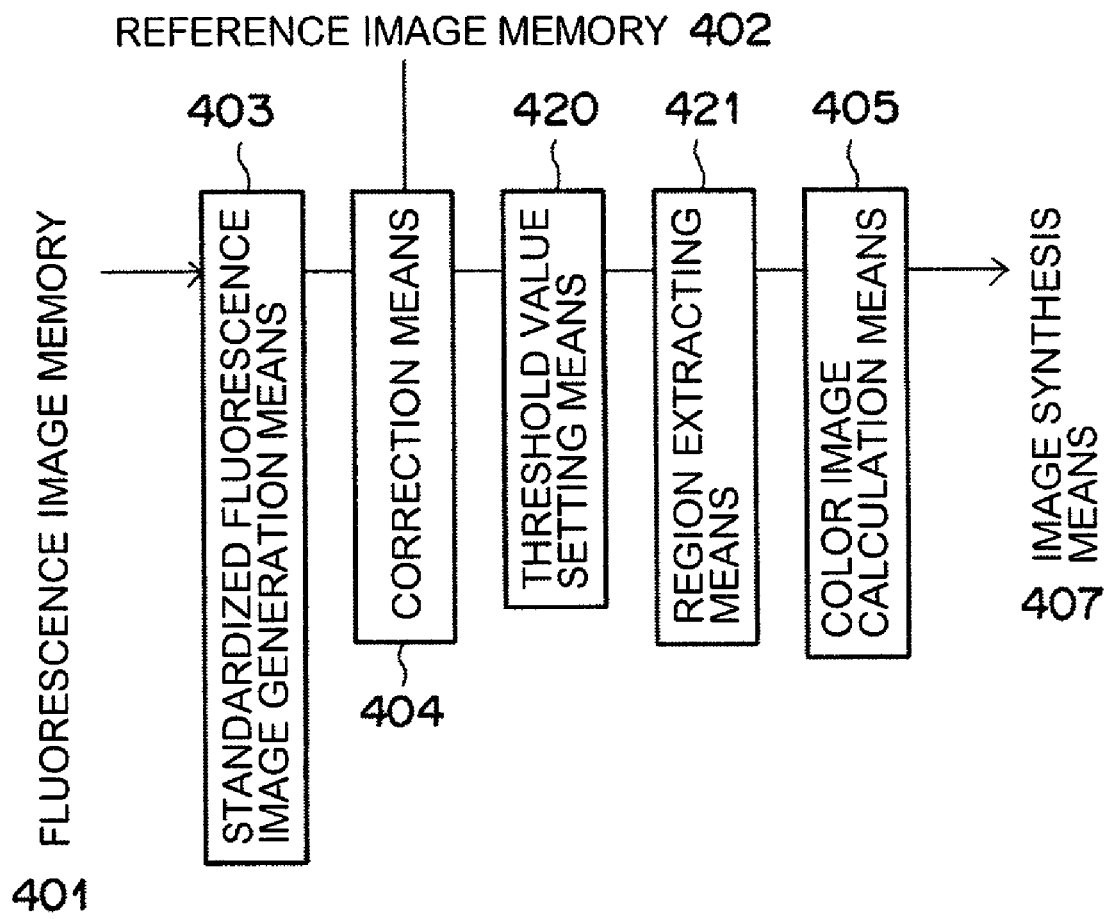
FIG. 7 is a structural diagram of the means employed in the case that a corrected calculated standardized value is calculated for a living tissue by employing an s number of correction functions corresponding to each living tissue of the aforementioned s steps; the aforementioned threshold values are employed to extract the regions of living tissue corresponding to each of the s steps from the s number of corrected standardized images; different color images are assigned for each of the s number of regions, thereby generating color images.
Figure 8:
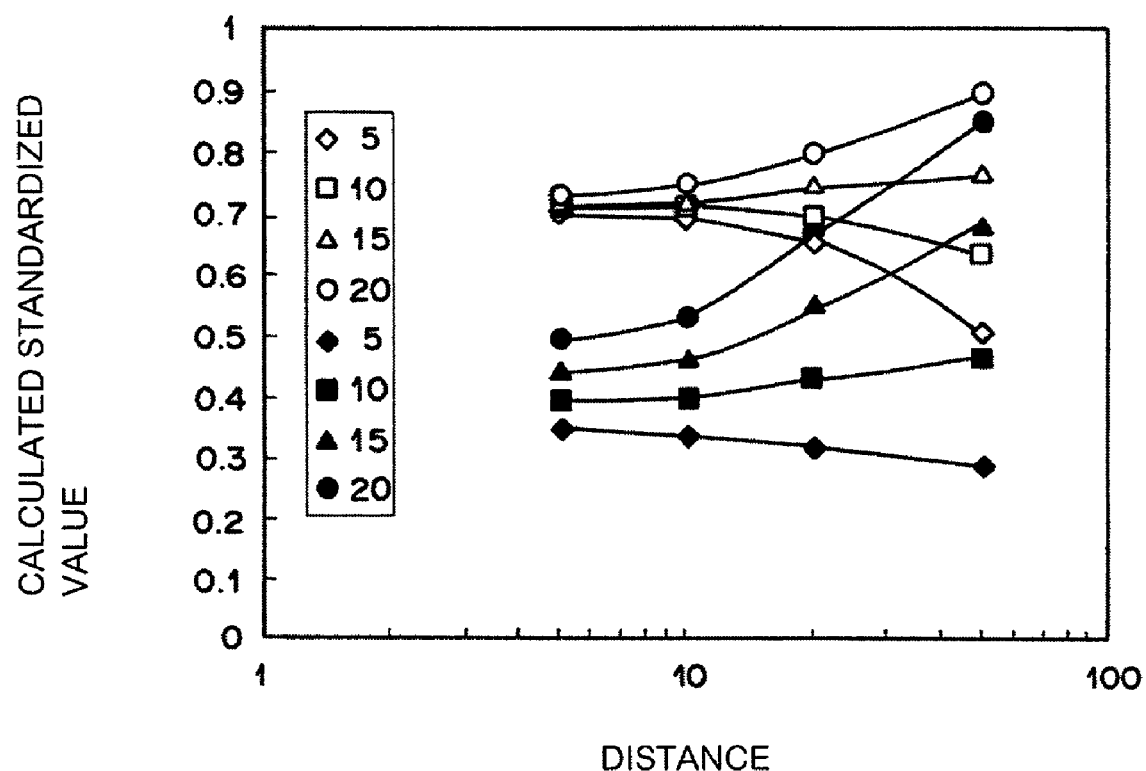
FIG. 8 is a graph that shows the relationship between calculated standardized values and the distance between a detection means and living tissue when the calculated standardized values are derived for normal tissue and diseased tissue by adding an offset.

In the first and second embodiments described above, a correction function is derived based on normal or diseased tissue, a corrected calculated standardized value is calculated employing the correction function thus derived, a threshold value is set based on the corrected calculated standardized value, and a Boolean judgment regarding the normal/diseased state of living tissue is made. However, a method may be adopted wherein the degree of disease progression of a diseased portion of living tissue is divided into s steps; a correction function is derived for living tissue corresponding to each of the s steps; an s number of corrected calculated standardized values, which are to be reference values, are calculated based on each of the s number of correction functions; and threshold values are set based on each of the s number of corrected calculated standardized values. In this case, a corrected calculated standardized value is calculated for an imaged target tissue by employing the s number of correction functions corresponding to each living tissue of the aforementioned s steps. The aforementioned threshold values are employed to extract the regions of living tissue corresponding to each of the s steps from the s number of corrected standardized images. Different color images are assigned for each of the s number of regions, and these color images are displayed superimposed on one another. In the case that this method is to be applied to the first embodiment, for example, a threshold setting means 420 and a region extracting means 421 can be provided between the correction means 404 and the color image calculation means 405 as shown in FIG. 7, and the regions corresponding to the living tissue of s steps output from the color image calculation means 405 can be superimposed by the image synthesis means 407.

In the first and second embodiments, a correction function is calculated by employing a normal portion of living tissue or a diseased portion of living tissue. However, living tissue of a plurality of patients may be utilized as this living tissue. Further, the correction function may be calculated and set prior to actual image diagnosis, or may be calculated and set or renewed during actual image diagnosis.

In the first and second embodiments, a single monitor is used to switch between display of a synthesized image and a standard image, or between display of a color image and a standard image. However, a separate monitor may be provided for displaying each of the above images. Further, the method of switching between display modes is not limited to the footswitch described in the above embodiments, but may be performed automatically in a time sequential manner by the control computer.

In addition, the GaN semiconductor laser 114 and the white light source 111 are structured as separate elements in the first and second embodiments. However, a single light source may serve as both an excitation light source and a white light source by utilizing an appropriate optical transmittance filter.

Further, an excitation light source that emits light having a wavelength within the range of 400 nm–420 nm may be selected.

In the first and second embodiments, the application of the standardized image generation method of the present invention in the case that a standardized image is generated based on fluorescence emitted by living tissue upon irradiation thereof by an excitation light has been described. However, the standardized image generation method of the present invention is not limited to standardized image generation based on emitted fluorescence as described above. For example, the standardized image generation method of the present invention may be applied in the case that the degree of oxygen saturation of living tissue is calculated based on reflected light reflected by living tissue upon the irradiation thereof with a white light, and a standardized image is generated based on the degree of oxygen saturation. The specifics of this case will be described below.

First, the method of calculating the degree of oxygen saturation will be described. White light is irradiated onto living tissue 9 from the endoscope insertion portion 100 of a fluorescence endoscope like that described above. Next, by imaging the reflected light reflected by the living tissue with an imaging element via bandpass filters of differing wavelength bandwidths $\lambda 1$ and $\lambda 2$, reflectance images r1 and r2 of different wavelength bandwidths $\lambda 1$ and $\lambda 2$, respectively, are obtained. Then, the degree of light absorption is calculated for each pixel of the two reflectance images r1 and r2, based on each of the pixel values thereof and the intensity of the white light irradiated onto the living tissue.

Here, the degree of light absorption changes corresponding to the degree of oxygen saturation of the living tissue. Therefore, the degree of oxygen saturation may be calculated from the aforementioned degree of light absorption. However, the aforementioned degree of light absorption changes due to the pulse of the living tissue. Accordingly, a heart rate monitor, for example, is provided; a time T1 when the degree of light absorption is at its maximum and a time T2 when the degree of light absorption is at its minimum, for example, is derived based on the pulse measured by the heart rate monitor; the difference between the degree of light absorption at time T1 and T2 is calculated; and the degree of oxygen saturation is calculated based on this difference.

In other words, $I\lambda 1(T1)$, which is the degree of light absorption for light of wavelength bandwidth $\lambda 1$ at time T1 based on image r1 is derived for each pixel thereof; $I\lambda 2(T1)$, which is the degree of light absorption for light of wavelength bandwidth $\lambda 2$ at time T1 based on image r2 is derived for each pixel thereof; $I\lambda 1(T2)$, which is the degree of light absorption for light of wavelength bandwidth $\lambda 1$ at time T2 based on image r1' is derived for each pixel thereof; $I\lambda 2(T2)$, which is the degree of light absorption for light of wavelength bandwidth $\lambda 2$ at time T2 based on image r2' is derived for each pixel thereof; and the difference $\Delta I\lambda 1$ and the difference $\Delta I\lambda 2$ is derived as follows:

$$\Delta I\lambda 1 = I\lambda 1(T1) - I\lambda 1(T2)$$

$$\Delta I\lambda 2 = I\lambda 2(T1) - I\lambda 2(T2)$$

Then, the degree of oxygen saturation $SaO_2$ can be derived based on $\Delta I\lambda 1$, which is the difference over time of the degree of light absorption for wavelength bandwidth $\lambda 1$, and $\Delta I\lambda 2$, which is the difference over time of the degree of light absorption for wavelength bandwidth $\lambda 2$ by the following equation.

$$SaO_2 = f(\Phi 12)$$

Wherein $\Phi 12 = \Delta I\lambda 1/\Delta I\lambda 2$. Note that f is a function which has been obtained based on the relationship between $\Phi 12$, which has been experimentally obtained, and $SaO_2$.

Here, the differences $\Delta I\lambda 1$ and $\Delta I\lambda 2$ are extremely small values, similar to the fluorescence described earlier. Therefore, if $\Phi 12$ is derived from these extremely small values, the degree of oxygen saturation $SaO_2$ calculated therewith, and the resulting image is displayed, the image will have a poor S/N ratio. Accordingly, adding an offset to derive $\Phi 12'$ as shown below in a similar manner to that when displaying a fluorescence image, for example, may be considered.

$$\Phi 12' = \Delta I\lambda 1/(\Delta I\lambda 2 + os3)$$

Here, os3 represents an offset value.

However, in the case that $\Phi 12'$ is derived by adding the offset as shown above, in a similar manner to that in the case of calculating a standardized fluorescence image by adding an offset to a fluorescence image, the value of $\Phi 12'$ differs according to the distance between the distal end of the endoscope insertion portion 100 and the living tissue. Therefore, the proper indication of the degree of oxygen saturation of living tissue based on $\Phi 12'$ is difficult. Accordingly, in a similar manner to that of the above described embodiments, $\Phi 12'$ is corrected with a correction function, the degree of oxygen saturation $SaO_2$ is calculated based on this corrected value, then displayed as an image. Thereby, an image that properly represents the degree of oxygen saturation, independent of the distance between the distal end of the endoscope insertion portion 100 and the living tissue, can be displayed. Further, as the correction function, Equation 6 below can be utilized, and $\Phi 12'$ can be corrected by performing calculations according to Equation 7 and Equation 8 below.

$$(Wir + os4)/Wir \qquad \text{Equation 6:}$$

Here, Wir represents the degree of light absorption when living tissue is irradiated with reference light, and os4 represents a correction coefficient.

$$\{\Delta I\lambda 1/(\Delta I\lambda 2 + os3) \times (Wir + os4)/Wir\} \qquad \text{Equation 7:}$$

$$os4 = os3 \times hir/hw \qquad \text{Equation 8:}$$

Here, hir represents the degree of light absorption when living tissue is irradiated with reference light divided by the distance between the distal end of the endoscope insertion portion 100 and living tissue 9, and hw represents $\Delta I\lambda 2$ divided by the distance between the distal end of the endoscope insertion portion 100 and living tissue 9.

The correction function to be utilized is not limited to that described in Equation 7. Alternate correction functions such as those described in the previous embodiments may be utilized.

As the method of obtaining the reflectance images r1 and r2 of different wavelength bandwidths $\lambda 1$ and $\lambda 2$, respectively, one can be employed wherein a planar sequential filter composed of bandpass filters for wavelength bandwidths $\lambda 1$ and $\lambda 2$ is utilized in order to obtain the two reflectance images r1 and r2 in a time sequential manner. Alternatively, a method wherein a mosaic filter composed of bandpass filters for wavelength bandwidths $\lambda 1$ and $\lambda 2$ is utilized in order to obtain the two reflectance images r1 and r2 in a simultaneous manner.

The obtainment of the reflectance images r1 and r2 may also be performed at the time that a standard image is obtained by irradiating living tissue with white light.

What is claimed is:

1. A method of standardized image generation comprising the steps of:
   irradiating living tissue with light;
   detecting images of mutually different wavelength bandwidths based on reradiated light generated from said living tissue by said irradiation with said light with an image detection means;
   adding a desired offset to at least one of said images of mutually different wavelength bandwidths; and
   generating a standardized imaged based on the ratio of said images of mutually different wavelength bandwidths, at least one of which a desired offset has been added to; wherein
   a predetermined correction function is employed for performing a distance correction on said standardized image, which corrects for the amount of fluctuation of said standardized image caused by the distance between said living tissue and said image detection means, thereby generating a corrected standardized image,
   said predetermined correction function is calculated based on at least one of a wide bandwidth image and a narrow bandwidth image and
   the wide bandwidth image and the narrow bandwidth image are of a living tissue for which a diseased state is known.

2. A method of standardized fluorescence image generation comprising the steps of:
   irradiating living tissue with excitation light;
   detecting fluorescence images of mutually different wavelength bandwidths based on fluorescent light generated from said living tissue by said irradiation with said excitation light with a fluorescence image detection means;
   adding a desired offset to at least one of said fluorescence images of mutually different wavelength bandwidths; and
   generating a standardized fluorescence image based on the ratio of said fluorescence images of mutually different wavelength bandwidths, at least one of which a desired offset has been added to; wherein
   a predetermined correction function is employed for performing a distance correction on said standardized image, which corrects for the amount of fluctuation of said standardized fluorescence image caused by the distance between said living tissue and said fluorescence image detection means, thereby generating a corrected standardized fluorescence image;
   said predetermined correction function is calculated based on at least one of a wide bandwidth image and a narrow bandwidth image and
   the wide bandwidth image and the narrow bandwidth image are of a living tissue for which a diseased state is known.

3. A method of standardized fluorescence image generation as defined in claim 2, wherein said fluorescence images of mutually different wavelength bandwidths are a narrow bandwidth fluorescence image and a wide bandwidth fluorescence image.

4. A method of standardized fluorescence image generation comprising the steps of:
   irradiating living tissue with excitation light;
   detecting fluorescence images of mutually different wavelength bandwidths based on fluorescent light generated from said living tissue by said irradiation with said excitation light with a fluorescence image detection means;
   adding a desired offset to at least one of said fluorescence images of mutually different wavelength bandwidths; and
   generating a standardized fluorescence image based on the ratio of said fluorescence images of mutually different wavelength bandwidths, at least one of which a desired offset has been added to; wherein
   a predetermined correction function is employed for performing a distance correction on said standardized image, which corrects for the amount of fluctuation of said standardized fluorescence image caused by the distance between said living tissue and said fluorescence image detection means, thereby generating a corrected standardized fluorescence image,
   said fluorescence images of mutually different wavelength bandwidths are a narrow bandwidth fluorescence image and a wide bandwidth fluorescence image, and
   said correcting function is calculated based on at least one of a wide bandwidth fluorescence image and a narrow bandwidth fluorescence image of a living tissue for which a diseased state is known.

5. A method of standardized fluorescence image generation comprising the steps of:
   irradiating living tissue with excitation light;
   detecting fluorescence images of mutually different wavelength bandwidths based on fluorescent light generated from said living tissue by said irradiation with said excitation light with a fluorescence image detection means;
   adding a desired offset to at least one of said fluorescence images of mutually different wavelength bandwidths; and
   generating a standardized fluorescence image based on the ratio of said fluorescence images of mutually different wavelength bandwidths, at least one of which a desired offset has been added to; wherein
   a predetermined correction function is employed for performing a distance correction on said standardized image, which corrects for the amount of fluctuation of said standardized fluorescence image caused by the distance between said living tissue and said fluorescence image detection means, thereby generating a corrected standardized fluorescence image, said fluorescence images of mutually different wavelength bandwidths are a narrow bandwidth fluorescence image and a wide bandwidth fluorescence image and said method of standardized fluorescence image generation further comprises the steps of:

irradiating a predetermined living tissue, for which a diseased state is known, with a reference light;

detecting a reference image formed of the reflected light reflected by said living tissue with a reference image detection means; and calculating said correcting function based on said reference image.

6. A method of standardized fluorescence image generation as defined in claim 5, wherein said correction function is expressed by the equation:

(nir+os2)/nir and said corrected standardized fluorescence image is expressed by the equation:

{n/(w+os1)}×{(nir+os2)/nir} where n is the narrow bandwidth fluorescence image; w is the wide bandwidth fluorescence image; nir is the reference image; os1 is the offset, os2 is the correction coefficient, os2=os1×knir/kw; knir is the reference image divided by the distance between the living tissue and the reference image detection means; and kw is the wide bandwidth fluorescence image divided by the distance between the living tissue and the fluorescence image detection means.

7. A method of standardized fluorescence image generation as defined in claim 6, wherein said os2 is calculated based on said knir and said kw corresponding to a normal portion of living tissue.

8. A method of standardized fluorescence image generation as defined in claim 6, wherein said os2 is calculated based on said knir and said kw corresponding to a diseased portion of living tissue.

9. A method of standardized fluorescence image generation as defined in claim 6, further comprising the steps of:

dividing the degree of diseased progression of a diseased portion of living tissue into s steps;

deriving knir and kw for each of said s steps; and calculating said os2 based on each of said knir and said kw; wherein s represents a natural number greater than or equal to 2.

10. A method of standardized fluorescence image generation as defined in claim 9, wherein:

an s number of said corrected standardized fluorescence images, which are to become reference corrected standardized fluorescence images, are calculated by employing an s number of said correction functions based on said os2 corresponding to each living tissue of said s steps to perform said distance correction to said standardized fluorescence images for each of said s steps;

a threshold value is set based on said s number of reference corrected standardized fluorescence images;

while on the other hand an s number of corrected standardized fluorescence images are calculated by employing said s number of correction functions to perform said distance correction to said standardized fluorescence images of living tissue;

a region for each of said living tissue of said s steps is extracted by employing said threshold value on said s number of corrected standardized fluorescence images; and said extracted regions are displayed superimposed on one another.

11. A standardized image generating apparatus comprising: a light emitting means for irradiating living tissue with light;

an image detection means for detecting images of mutually different wavelength bandwidths based on reradiated light generated from said living tissue by said irradiation with said light;

a standardized image generating means for adding a desired offset to at least one of said images of mutually different wavelength bandwidths and generating a standardized image based on the ratio of said images of mutually different wavelength bandwidths, at least one of which a desired offset has been added to; and a correction means for employing a predetermined correction function on said standardized image to perform a distance correction, which corrects for the amount of fluctuation of said standardized image caused by the distance between said living tissue and said image detection means, thereby generating a corrected standardized image, wherein said predetermined correction function is calculated based on at least one of a wide bandwidth fluorescence image and a narrow bandwidth fluorescence image and the wide bandwidth fluorescence image and the narrow bandwidth fluorescence image are of a living tissue for which a diseased state is known.

12. A standardized fluorescence image generating apparatus comprising:

an excitation light emitting means for irradiating living tissue with excitation light;

a fluorescence image detection means for detecting fluorescence images of mutually different wavelength bandwidth based on fluorescent light generated from said living tissue by said irradiation with said excitation light;

a standardized fluorescence image generating means for adding a desired offset to at least one of said fluorescence images of mutually different wavelength bandwidths and generating a standardized fluorescence image based on the ratio of said fluorescence images of mutually different wavelength bandwidths, at least one of which a desired offset has been added to; and a correction means for employing a predetermined correction function on said standardized image to perform a distance correction, which corrects for the amount of fluctuation of said standardized fluorescence image caused by the distance between said living tissue and said fluorescence image detection means, thereby generating a corrected standardized fluorescence image, Wherein said predetermined correction function is calculated based on at least one of a wide bandwidth fluorescence image and a narrow bandwidth fluorescence image and the wide bandwidth image and the narrow bandwidth image are of a living tissue for which a diseased state is known.

13. A standardized fluorescence image generating apparatus as defined in claim 12, wherein said fluorescence images of mutually different wavelength bandwidths are a narrow bandwidth fluorescence image and a wide bandwidth fluorescence image.

14. A standardized fluorescence image generating apparatus comprising:

an excitation light emitting means for irradiating living tissue with excitation light;

a fluorescence image detection means for detecting fluorescence images of mutually different wavelength bandwidth based on fluorescent light generated from said living tissue by said irradiation with said excitation light;

a standardized fluorescence image generating means for adding a desired offset to at least one of said fluorescence images of mutually different wavelength bandwidths and generating a standardized fluorescence image based on the ratio of said fluorescence images of mutually different wavelength bandwidths, at least one of which a desired offset has been added to; and a correction means for employing a predetermined correction function on said standardized image to perform a distance correction, which corrects for the amount of fluctuation of said standardized fluorescence image caused by the distance between said living tissue and said fluorescence image detection means, thereby generating a corrected standardized fluorescence image, wherein said fluorescence images of mutually different wavelength bandwidths are a narrow bandwidth fluorescence image and a wide bandwidth fluorescence image and said correcting function is calculated based on at least one of a wide bandwidth fluorescence image and a narrow bandwidth fluorescence image of a living tissue for which a diseased state is known.

15. A standardized fluorescence image generating apparatus comprising:

an excitation light emitting means for irradiating living tissue with excitation light;

a fluorescence image detection means for detecting fluorescence images of mutually different wavelength bandwidth based on fluorescent light generated from said living tissue by said irradiation with said excitation light;

a standardized fluorescence image generating means for adding a desired offset to at least one of said fluorescence images of mutually different wavelength bandwidths and generating a standardized fluorescence image based on the ratio of said fluorescence images of mutually different wavelength bandwidths, at least one of which a desired offset has been added to; and a correction means for employing a predetermined correction function on said standardized image to perform a distance correction, which corrects for the amount of fluctuation of said standardized fluorescence image caused by the distance between said living tissue and said fluorescence image detection means, thereby generating a corrected standardized fluorescence image, wherein said fluorescence images of mutually different wavelength bandwidths are a narrow bandwidth fluorescence image and a wide bandwidth fluorescence image, said standardized fluorescence image generating apparatus further comprising:

a reference light emitting means for irradiating a predetermined living tissue, for which a diseased state is known, with a reference light; and a reference image detection means for detecting a reference image formed of the reflected light reflected by said living tissue; wherein said correcting function is calculated based on said reference image.

16. A standardized fluorescence image generating apparatus as defined in claim 15, wherein said correction function is expressed by the equation:

$$(nir+os2)/nir$$

and said corrected standardized fluorescence image is expressed by the equation:

$$\{n/(w+os1)\} \times \{(nir+os2)/nir\}$$

where n is the narrow bandwidth fluorescence image; w is the wide bandwidth fluorescence image; nir is the reference image; os1 is the offset, os2 is the correction coefficient, $os2 = os1 \times knir/kw$; knir is the reference image divided by the distance between the living tissue and the reference image detection means; and kw is the wide bandwidth fluorescence image divided by the distance between the living tissue and the fluorescence image detection means.

17. A standardized fluorescence image generating apparatus as defined in claim 16, wherein said os2 is calculated based on said knir and said kw corresponding to a normal portion of living tissue.

18. A standardized fluorescence image generating apparatus as defined in claim 16, wherein said os2 is calculated based on said knir and said kw corresponding to a diseased portion of living tissue.

19. A standardized fluorescence image generating apparatus as defined in claim 16, wherein:

the degree of disease progression of a diseased portion of living tissue is divided into s steps;

knir and kw are derived for each of said s steps; and said os2 is calculated based on each of said knir and said kw; wherein s represents a natural number greater than or equal to 2.

20. A standardized fluorescence image generating apparatus as defined in claim 19, wherein:

an s number of said corrected standardized fluorescence images, which are to become reference corrected standardized fluorescence images for each living tissue of said s steps, are calculated by employing an s number of said correction functions based on said os2 corresponding to each living tissue of said s steps to perform said distance correction to said standardized fluorescence images for each of said s steps; further comprising a threshold value setting means for setting a threshold value based on said s number of reference corrected standardized fluorescence images;

a region extracting means for extracting a region for each living tissue of said s steps by employing said threshold value on s number of corrected standardized fluorescence images calculated by said correction means employing said s number of correction functions; and a display means for displaying said regions superimposed on one another.

21. A method of standardized fluorescence image generation comprising the steps of:

irradiating living tissue with excitation light;

detecting fluorescence images of mutually different wavelength bandwidths based on fluorescent light generated from said living tissue by said irradiation with said excitation light with a fluorescence image detection means;

adding a desired offset to at least one of said fluorescence images of mutually different wavelength bandwidths; and generating a standardized fluorescence image based on the ration ratio of said fluorescence images of mutually different wavelength bandwidths, at least one of which a desired offset has been added to; wherein a predetermined correction function is employed for performing a distance correction on said standardized image, which corrects for the amount of fluctuation of said standardized fluorescence image caused by the distance between said living tissue and said fluorescence image detection means, thereby generating a corrected standardized fluorescence image, and said method of standardized fluorescence image generation further comprises the steps of:

irradiating a predetermined living tissue, for which a diseased state is known, with a reference light;

detecting a reference image formed of the reflected light reflected by said living tissue with a reference image detection means; and calculating said correcting function based on said reference image.

22. A standardized fluorescence image generating apparatus comprising:

an excitation light emitting means for irradiating living tissue with excitation light;

a fluorescence image detection means for detecting fluorescence images of mutually different wavelength bandwidth based on fluorescent light generated from said living tissue by said irradiation with said excitation light;

a standardized fluorescence image generating means for adding a desired offset to at least one of said fluorescence images of mutually different wavelength bandwidths and generating a standardized fluorescence image based on the ratio of said fluorescence images of mutually different wavelength bandwidths, at least one of which a desired offset has been added to;

a correction means for employing a predetermined correction function on said standardized image to perform a distance correction, which corrects for the amount of fluctuation of said standardized fluorescence image caused by the distance between said living tissue and said fluorescence image detection means, thereby generating a corrected standardized fluorescence image, a reference light emitting means for irradiating a predetermined living tissue, for which a diseased state is known, with a reference light; and a reference image detection means for detecting a reference image formed of the reflected light reflected by said living tissue; wherein said correcting function is calculated based on said reference image.

\* \* \* \* \*